US006372772B1

(12) United States Patent
Kirkpatrick et al.

(10) Patent No.: US 6,372,772 B1
(45) Date of Patent: Apr. 16, 2002

(54) INHIBITORS OF REDOX SIGNALING AND METHODS OF USING SAME

(75) Inventors: D. Lynn Kirkpatrick, Emerald Park (CA); Garth Powis, Tucson, AZ (US)

(73) Assignee: Prolx Pharmaceuticals Corporation, Pittsburgh, PA (US)

( * ) Notice: Subject to any disclaimer, the term of this patent is extended or adjusted under 35 U.S.C. 154(b) by 0 days.

(21) Appl. No.: 09/127,219

(22) Filed: Jul. 31, 1998

Related U.S. Application Data

(60) Provisional application No. 60/054,566, filed on Aug. 1, 1997.

(51) Int. Cl.[7] .................. A61K 31/415; A61K 31/42
(52) U.S. Cl. .................. 514/396; 514/397; 514/398; 514/399; 514/400; 514/375
(58) Field of Search .................. 514/396, 397, 514/398, 399, 400, 375

(56) References Cited

U.S. PATENT DOCUMENTS

| 5,633,274 A | 5/1997 | Halperin et al. ............ 514/405 |
| 5,645,988 A | 7/1997 | Vande Woude et al. ........ 435/6 |

FOREIGN PATENT DOCUMENTS

| WO | 98/00160 | 1/1998 |
| WO | 98/24472 | 6/1998 |
| WO | 98/29449 | 7/1998 |

OTHER PUBLICATIONS

Oblong et al, Cancer, Chemotherapy and Pharmacology, vol. 34, pp. 44–38, 1994.*
Dimmock et al, 109CA:109953, 1987.*
Cssady et al, 89CA:99714, 1994.*
Laurent, T.C. et al. Enzymatic Synthesis of deoxyribonucleotides VI. Isolation and Characterization of Thioredoxin, the Hydrogen Donor from *Escherichia coli* B. J. Biol. Chem. 239 (1964):3436–44.
Krohne–Enrich G. et al. Glutathione Reductase from Human Erythrocytes. Isolation of the Enzyme and sequence analysis of the redox–active peptide. Eur. J. Biochem. 80 (1971): 65–71.
Riondel, J. et al. Studies of antitumor activity of the culture filtrate of Hohenbuehel Geogenius (D.C. ex Fr.) Sing (Basidiomycete). Drug Research 31/2 (1981): 293–9.
Luthman, M. et al. Rat Liver Thioredoxin and Thioredoxin Reductase: Purification and Characterization. Biochemistry 21/26 (Dec. 21, 1982): 6628–33.
Grippo, J.F. et al. Evidence that the Endogenous Heat–Stable Glucocorticoid Receptor–Activating Factor is Thioredoxin. J. Biol. Chem. 258 (1983): 13658–64.
Holmgren, A. et al. Thioredoxin. Ann. Rev. Biochem. 54 (1985): 237–71.
Dimmock, J.R. et al. Eur. J. Med. Chem. 22 (1987): 545–551.

Kirkpatrick, D.L. Modification of Antitumor Disulfide cytotoxicity by Glutathione Depletion. Cancer Res. 47 (1987): 4391–95.
Silverman, R.B. et al. Reduced Thioredoxin: A Possible Physiological Cofactor for Vitamin K Epoxide Reductase. Further Support for an Active Site Disulfide. Biochem. Biophys. Res. Commun. 155 (1988): 1248–54.
Boyd, M.R. Status of Implementation of the NCI Human Tumor Cell in Line in vitro Primary Drug Screen. Proc Am. Assoc. Cancer Res. 30 (1989): 652–54.
Coshan–Gauthier, R. et al. Modulation of Disulfide Antitumor Activity in Balb/c mice through Glutathione Depletion. Exp. Cell Biol. 57 (1989): 273–80.
Cromlish, J.A. et al. Human Transcription Factor IIIC (TFIIIC). Purification, Polypeptide Structure, and the Involvement of Thiol Groups in Specific DNA Binding. J. Biol. Chem. 264 (1989): 18100–109.
Hart, D.J. et al. J. American Chem. Soc. 19 (1989): 7507–19.
Kirkpatrick, D.L. Kinetic Studies of the Interaction of Glutathione with Four Antitumor Disulfides: Possible Mechanism for cellular GSH depletion. Chem. Biol. Interact. 69 (1989): 225–34.
Paull, K.D. et al. Display and Analysis of Patterns of Differential Activity of Drugs Against Human Tumor Cell Lines: Development of Mean Graph and COMPARE Algorithm. Journal of the National Cancer Institute 81 (1989): 1088.
Kirkpatrick, D.L. et al. Inhibitory Effect of Cytotoxic Disulfides on membrane Na+/K+ ATPase. Biochem. Pharmacol. 39 (1990): 1484–87.
Lundstrom, J. et al. Protein Disulfide–isomerase is a Substrate for Thioredoxin reductase and has Thioredoxin–like Activity. J. Biol. Chem. 265 (1990): 9114–20.
Wakasugi, N. et al. Adult T–Cell Leukemia derived factor/thioredoxin produced by both human T–lymphotropic Virus Type 1 and Epstein–Barr virus–transformed lymphocytes, acts as an autocrine growth factor and synergized with interleukin–1 and interluken–2. Proc. Natl. Acad. Sci. USA 87 (1990): 8282–86.
Dimmock, J.R. et al. Evaluation of Some Mannich Bases of 1–aryl–lethanones and Related Ketones for Anticonvulsant Activities. Pharmazie 46/7 (Jul. 1991): 538–39.

(List continued on next page.)

*Primary Examiner*—Russell Travers
(74) *Attorney, Agent, or Firm*—Raymond A. Miller; Benesch, Friedlander, Coplan & Aronoff, LLP

(57) ABSTRACT

The present invention is directed to a composition or formulation which inhibits or interferes with cellular redox function, and method of using same to restore normal cellular function. More specifically, the composition of the present invention interferes with or inhibits abnormal cellular proliferation and//restores or cellular apoptosis.

4 Claims, 6 Drawing Sheets

OTHER PUBLICATIONS

Fujii, S. et al. Coexpression of Adult T–Cell Leukemia–derived factor, a Human Thioredoxin Homologue, and Human Papillomavirus DNA in Neoplastic Cervical Squamous Epithelium. Cancer 68 (1991):1583–91.

Monks, A. et al. Feasibility of a High–Flux Anticancer Drug Screen Using a Diverse Panel of Cultured Human Tumor Cell Lines. Journal of the National Cancer Institute 83 (1991): 757.

Yodoi, J. et al. ADF, a Growth–Promoting Factor Derived from Adult T–Cell Leukemia and Homologous to Thioredoxin: Involvement in Lymphocyte Immortalization by HTLV–1 and EBV. Adv. Cancer Res. 57 (1991): 381–411.

Ericson, M.L. et al. Secretion of Thioredoxin After in vitro Activation of Human B Cells. Lymphokine Cytokine Res. 11 (1992): 201–07.

Fountoulakis, M. et al. Unfolding Intermediates of the Extracellular Domain of the Interferon Gamma Receptor. J. Biol. Chem. 267 (1992): 7095–7100.

Kirkpatrick, D.L. et al. Effect of a Hypoxic Tumor Cell Cytotoxic Disulfide on the Membrane and DNA of Tumor Cells in Culture. Anticancer Drugs 3 (1992): 651–58.

Kirkpatrick, D.L. et al. Synthesis and Evaluation of Imidazolyl Disulfides for Selective Cytotoxicity to Hypoxic EMT6 Tumor Cells in vitro. Euro. J. Med. Chem. 27 (1992): 33–37.

Matthews, J.R. et al. Thioredoxin Regulates the DNA Binding Activity of NF–KappaB by Reduction of a Disulphide Bond Involving Cysteine 62. Nucleic Acids Res. 20 (1992): 3821–30.

Nakamura, H. et al. Expression and Growth–Promoting Effect of Adult T–Cell Leukemia–derived Factor. A Human Thioredoxin Homologue in Hepatocellular Carcinoma. Cancer 69 (1992): 2091–97.

Nishizuka, Y. et al. Intracellular Signaling by Hydrolysis of Phospholipids and Activation of Protein Kinase C. Science 258 (1992): 607.

Paull, K.D. e t al. Identification of Novel Antimitotic Agents acting at the Tubulin Level by Computer–Assisted Evaluation of Differential Cytotoxicity Data. Cancer Res. 52 (1992): 3892–3900.

Roschger, P. et al. J. Het. Chem. 29 (1992): 225–231.

Rubartelli, A. et al. Secretion of Thioredoxin by Normal and Neoplastic Cells Through a Leaderless Secretory Pathway. J. Biol. Chem. 267/34 (Dec. 5, 1992): 24161–64.

Oblong, J.E. et al. Purification of Human Thioredoxin Reductase: Properties and Characterization by Absorption and Circular Dichroism Spectroscopy. Biochemistry 32 (1993): 7271–77.

Wakelam, M.J.O. e t al. Phosphatidylcholiine Hydrolysis: A Multiple Messenger Generating System. Advances in Second Messenger and Phosphoprotein Research 28 (1993): 73–80.

Wang, Y. et al. Wild–type p53–triggered apoptosis is inhibited by bcl–2 in a v–myc–induced T–Cell Lymphoma Line. Oncogene 8 (1993): 3427–31.

Galter, D. et al. Distinct Effects of Glutathione Disulfide on the Nuclear Transcription Factors KappaB and the Activator Protein–1. Eur. J. Biochem. 221 (1994): 639–48.

Gasdaska, P.Y. et al. The Predicted Amino Acid Sequence of Human Thioredoxin is identical to that of the Autocrine Growth Factor Human Adult T–Cell Derived Factor (ADF): Thioredoxin mRNA is Elevated in Some Human Tumors. Biochem. Biophys. Acta 1218 (1994): 292–96.

Kirkpatrick, D.L. et al. Disulfide Cytotoxicity Under Hypoxia. Oncol. Res. 6/10–11 (1994): 545–52.

Lee. et al. Rhodamine Eflux patterns Predict P–Glycoprotein Substrates in the Natural Cancer Institute Drug Screen. Molecular Pharmacology 46 (1994): 627.

Oblong, J.E. et al. Site–directed Mutagenesis of Active Site cysteines in Human Thioredoxin Produces Competitive Inhibitors of Human Thioredoxin Reductase and Elimination of Mitogenic Properties of Thioredoxin. J. Biol. Chem. 269 (1994): 11714–720.

Oblong, J.E. et al. Reversible Inhibition of Human Thioredoxin Reductase Activity by Cytotoxic Alkyl 2–imidazoly Disulfide Analogues. Cancer Chemother. Pharmacol. 34 (1994): 434–38.

Powis, G. et al. The Thioredoxin/Thioredoxin Reductase Redox System and Control of Cell Growth. Oncol. Res. 6/10–11 (1994): 539–44.

Verentchikov A.N. et al. Reflecting time–of–flight mass spectrometer with an electrospray ion source and orthogonal extraction. Anal. Chem. 66 (1994): 126–133.

Gasdaska, J.R. et al. Cell Growth Stimulation by the Redox Protein Thioredoxin Occurs by a Novel Helper Mechanism. Cell Growth Differ. 6 (1995): 1642–50.

Gasdaska, P.Y. et al. Cloning and Sequencing in Human Thioredoxin reductase. FEBS Letters 373/1 (Oct. 5, 1995): 5–9.

Kirkpatrick, D.L. et al. Stimulation of Apoptosis by a Redox Active Disulfide. Proc. Am. Assoc. Cancer Res. 36 (1995): 2469.

Kuperus, M. et al. Interaction of Redox Active Disulfides with the Autocrine Growth Factor, Human Thioredoxin. Proc. Am. Assoc. Cancer Res. 36 (1995): 2541.

Orr, A. et al. "Waterbug" Dialysis. Biotechniques 19 (1995): 204–206.

Rubartelli, A. et al. High Rates of Thioredoxin Secretion Correlate with Growth Arrest in Hepatoma Cells. Cancer Res. 55 (1995): 675–80.

Berggren, M. et al. Thioredoxin and Thioredoxin Reductase Gene Expression in Human Tumors and Cell Lines, and the Effects of Serum Stimulation and Hypoxia. Anticancer Res. 16 (1996): 3459–66.

Borman, S. Combinatorial Chemists Focus on Small Molecules, Molecular Recognition and Automation. Chem. Eng. News 74 (1996): 29–64.

Gallegos, A. et al. Transfection with Human Thioredoxin Increases Cell Proliferation and a Dominant–Negative Mutant Thioredoxin Reverses the Transformed Phenotype of Human Breast Cancer Cells. Cancer Res. 56/24 (Dec. 15, 1996): 5765–70.

Gasdaska, J.R. et al. Oxidative Inactivation of Thioredoxin as a Cellular Growth Factor and Protection by CYS(73)→Ser Mutation. Biochem. Pharmacol. 52 (1996): 1741–47.

Gladyshev, V.N. et al. Selenocysteine, Identified as the Penultimate C–Terminal Residue in Human T–Cell Thioredoxin Reductase, Corresponds to TGA in the Human Placental Gene. Proc. Natl. Acad. Sci USA 93 (1996): 6146–47.

Kuo, Y.H. et al. 126CA:142020a abstract.

Powis, G. et al. Thioredoxin Redox Signaling: A Novel Target for Anti–cancer Drug Development. Anti–Cancer Drugs 7/3 (1996): 121–26.

Weichsel, A. et al. Crystal Structures of Reduced, Oxidized and Mutated Human Thioredoxins: Evidence for a Regulatory Homodimer. Structure 4 (1996): 735–751.

Baker, R.W. et al. Chem. Commun. (1997): 451–452.

Kapadia, G.H. et al. Anti–tumor Promoting Effects of Naphthoquinone Derivatives on Short Epstein–Barr Early Antigen Activation Assay and in Mouse Skin Carcinogenesis. Cancer Letters 113/1–2 (Feb. 26, 1997): 47–53.

Kirkpatrick, D.L. et al. Antitumor Activity of Inhibitors of a Novel Signaling Pathway: Thioredoxin/Thioredoxin Reductase. Proc. Am. Assoc. Cancer Res. 38 (1997): 4115.

Kirkpatrick, D.L. et al. Redox Control as a Target for Anticancer Drug Development. Current Pharmaceutical Design 3 (1997): 305–22.

Kirkpatrick, D.L. et al. Redox Active Disulfides: The Thioredoxin System as a Drug Target. Oncology Research 9 (1997): 351–56.

Kunkel, M.W. et al. Cell Line–Directed Screening Assay for Inhibitors of Thioredoxin Reductace Signaling as Potential Anti–Cancer Drugs. Anti–Cancer Drug Design 12/8 (Dec. 1997) 659–70.

Kuo, Y.H. et al. Cytotoxic Constituents from the Stems of Diospyros Maritima. Planta–Medica 63 (Aug. 1997): 363–365.

Spyrout, G. et al. Cloning and Expression of a Novel Mammalian Thioredoxin. J Biol. Chem. 272/5 (1997):2936–41.

Weinstein, J.N. et al. An Information–Intensive Approach to the Molecular Pharmacology of Cancer. Science 275 (1997): 343.

Baker, R.W. et al. Synthesis and Absolute Configuration of Axially Chiral Binaphthoquinones. Australian Journal of Chemistry 51 (1998): 255–266.

Kirkpatrick, D.L. et al. Mechanisms of Inhibition of the Thioredoxin Growth Factor System by Antitumor 2–Imidazolyl Disulfides. Biochemical Pharmacology 55/7 (Apr. 1, 1998): 987–94.

Mebe, P.P. et al. Pentacyclic Triterpenes and Naphthoquinones from Euclea Divinorum. Phytochemistry. 47 (1998): 311–313.

* cited by examiner

131233

665102

631136

140377

603084

382007

635002

620358

657028

661221

622188

350629

102817

626162

655897

267461

627124

610187

624982

664951

277293

634761

608972

664271

665878

625814

264054

652257

661225

647546

637828

655305

641396

662781

626678

668262

SEQUENCE LISTING

<160> NUMBER OF SEQ ID NOS: 2

<210> SEQ ID NO 1
<211> LENGTH: 2191
<212> TYPE: DNA
<213> ORGANISM: Homo sapiens

<400> SEQUENCE: 1

| | | | | | |
|---|---|---|---|---|---|
| gaattcgggc | cgggtggtga | tcttcagcaa | gagctactgt | ccccatagta | ctcgggtgaa | 60 |
| agaactcttt | tcttctttgg | gagtcgaatg | taatgtcttg | gaacttgatc | aagttgatga | 120 |
| tggggccagg | gttcaagaag | tgctgtcaga | atcactaat | cagaaaactg | tgcccaatat | 180 |
| tttcgtgaat | aaagtgcatg | taggtggatg | tgaccaaact | ttccaggcat | atcagagtgg | 240 |
| tttgttacgg | aagctccttc | aggaagattt | ggcatatgat | tatgatctca | tcatcatcgg | 300 |
| tggtggttct | ggaggccttt | catgtgcgaa | ggaagctgcc | attttgggaa | agaaagttat | 360 |
| ggtgctagac | tttgttgtcc | cgtcacctca | gggcacatcc | tggggtcttg | gtggcacttg | 420 |
| tgtaaatgta | ggttgtattc | ctaagaaatt | gatgcatcag | gctgcccttt | tggggcaggc | 480 |
| attatgtgac | tcaaggaaat | ttggctggga | atataatcaa | caagtgaggc | acaactggga | 540 |
| gacaatgaca | aaagcgattc | agaaccacat | cagctctcta | aactgggct | acaggttgtc | 600 |
| tctgagggaa | aaggctgtgg | cctatgtcaa | ttcctatgga | gaatttgttg | aacatcataa | 660 |
| aataaaggca | accaataaaa | aaggacagga | gacttattat | actgctgcac | agtttgtcat | 720 |
| agcaacgggt | gaaaggccac | ggtatttagg | aatccaagga | gataaagaat | actgtattac | 780 |
| tagtgatgac | cttttttctc | tgccttattg | ccctggcaaa | acattagtgg | tgggtgcctc | 840 |
| ttatgttgcc | ctggagtgtg | cagggtttct | ggctggcttt | ggcctagatg | tcacagttat | 900 |
| ggtacgctca | atccttctcc | gtggcttcga | ccaagaaatg | gcagaaaaag | tgggttccta | 960 |
| catggagcag | catggtgtga | agttcctacg | gaaattcata | cctgtgatgg | ttcaacagtt | 1020 |
| ggagaaaggt | tcacctggaa | agctgaaagt | gttggctaaa | tccactgaag | gagaaacaat | 1080 |
| tgaaggagtc | tataacacag | ttttgttagc | tattggtcgt | gactcctgta | caaggaaaat | 1140 |
| aggcttggag | aagattggtg | tcaaaattaa | tgagaagagt | ggaaaaatac | ctgtaaatga | 1200 |
| tgtggaacag | accaatgtgc | catatgtcta | tgctgttggt | gatattttgg | aggataagcc | 1260 |
| agagctcact | cctgtcgcca | tacagtcagg | caagctgcta | gctcagagac | tttttggggc | 1320 |
| ctctttagaa | aagtgtgatt | atattaatct | tccgactaca | gtgtttactc | ctctggagta | 1380 |
| tggttgctgt | ggattatctg | aagagaaagc | tattgaagta | tataaaaaag | agaatctaga | 1440 |
| aatatatcat | agtttgttct | ggcctcttga | atggacagta | gctggcagag | agaacaacac | 1500 |
| ttgttacgca | aagataatct | gcaataaatt | cgaccatgat | cgggtgatag | gatttcatat | 1560 |
| tcttggacca | aacgccggtg | aggttaccca | aggatttgca | gctgcaatga | aatgtgggct | 1620 |
| cacaaaacag | ctacttgatg | acaccattgg | aattcacccc | acatgtgggg | aggtgttcac | 1680 |
| gactttggaa | atcacaaagt | cgtcaggact | agacatcact | cagaaaggct | gctgaggcta | 1740 |
| ggcctgctgc | tgtttagttc | tccttgtcat | attctcattt | ctctcaaaga | taagaatgct | 1800 |
| ctcggataaa | atgagcctgt | gctcatgaca | gctgctctgt | tactcaggga | ccagtgcagg | 1860 |
| gctgtcttac | gacacttaga | tgagaaagta | gacaaggaaa | gaggacagca | gtgggcatct | 1920 |

-continued

| | |
|---|---|
| gccttgtggt cttgctgaca gcgagaagca gtgggactgc ttccttgacg ccttagcttg | 1980 |
| gagccccgtt atgaggtgag ccaaggctga ctctcgcaag ccaggactga gcttccctcg | 2040 |
| gaaagacctt tgagtggcac cattcaccta agttagcttt tctggtcgct attgttttta | 2100 |
| tccccttttgt tgttgtttc tgtgaaaata tattttcagt taagaaatgc aaatatctta | 2160 |
| atgagtggta aaaaaaaaaa aaccggaatt c | 2191 |

<210> SEQ ID NO 2
<211> LENGTH: 2187
<212> TYPE: DNA
<213> ORGANISM: Homo sapiens

<400> SEQUENCE: 2

| | |
|---|---|
| gaattccgat tccccacacc ctatcccagt gttccaccct aggtctgaag gccccgccc | 60 |
| cgaatccggc cgcattcggc cccggtctag ccagcgctct cacctctccc gcgacggccc | 120 |
| gccgggactg gacccgcccc ggtccggcgc aggcagcgcg gcgggcagcc ctagctgccc | 180 |
| cagaagcccc acgacgatgg cggcaatggc ggtggcgctg cggggattag gagggcgctt | 240 |
| ccggtggcgg acgcaggccg tggcgggcgg ggtgcggggc gggcgcgggg cgcagcagc | 300 |
| aggtcagcgg gactatgatc tcctggtggt cggcggggga tctggtggcc tggcttgtgc | 360 |
| caaggaggcc gctcagctgg gaaggaaggt gtccgtggtg gactacgtgg aaccttctcc | 420 |
| ccaaggcacc cggtggggcc ttggcggcac ctgcgtcaac gtgggctgca tccccaagaa | 480 |
| gctgatgcac caggcggcac tgctgggagg cctgatccaa gatgccccca actatggctg | 540 |
| ggaggtggcc cagcccgtgc cgcatgactg gaggaagatg gcagaagctg ttcaaaatca | 600 |
| cgtgaaatcc ttgaactggg gccaccgtgt ccagcttcag gacagaaaag tcaagtactt | 660 |
| taacatcaaa gccagctttg ttgacgagca cacggtttgc ggcgttgcca aggtgggaa | 720 |
| agagattctg ctgtcagccg atcacatcat cattgctact ggagggcggc cgagataccc | 780 |
| cacgcacatc gaaggtgcct tggaatatgg aatcacaagt gatgacatct tctggctgaa | 840 |
| ggaatcccct ggaaaaactg gggtggtcgg ggccagctat gtgggccctgg agtgtgctgg | 900 |
| cttcctcacc gggattgggc tggacaccac catcatgatg cgcagcatcc cctccgcgg | 960 |
| cttcgaccag caaatgtcct ccatggtcat agagcacatg gcatctcatg cacccggtt | 1020 |
| cctgaggggc tgtgccccct cgcgggtcag gaggctccct gatggccagc tgcaggtcac | 1080 |
| ctgggaggac agcaccaccg gcaaggagga cacgggcacc tttgacaccg tcctgtgggc | 1140 |
| cataggtcga gtcccagaca ccagaagtct gaatttggag aaggctgggg tagatactag | 1200 |
| ccccgacact cagaagatcc tggtggactc ccgggaagcc acctctgtgc ccacatcta | 1260 |
| cgccattggt gacgtggtgg aggggcggcc tgagctgaca cccatagcga tcatggccgg | 1320 |
| gaggctcctg gtgcagcggc tcttcggcgg tcctcagat ctgatggact acgacaatgt | 1380 |
| tcccacgacc gtcttcaccc cgctggagta tggctgtgtg gggctgtccg aggaggaggc | 1440 |
| agtggctcgc cacgggcagg agcatgttga ggtctatcac gcccattata aaccactgga | 1500 |
| gttcacggtg gctggacgag atgcatccca gtgttatgta aagatggtgt gcctgaggga | 1560 |
| gcccccacag ctggtgctgg gcctgcattt ccttggcccc aacgcaggcg aagttactca | 1620 |
| aggatttgct ctggggatca agtgtggggc ttcctatgcg caggtgatgc ggaccgtggg | 1680 |
| tatccatccc acatgctctg aggaggtagt caagctgcgc atttccaagc gctcaggcct | 1740 |
| ggaccccacg gtgacaggct gctgagggta agcgccatcc ctgcaggcca gggcacacgg | 1800 |
| tgcgcccgcc gccagctcct cggaggccag acccaggatg gctgcaggcc aggtttgggg | 1860 |

-continued

```
ggcctcaacc ctctcctgga gcgcctgtga gatggtcagc gtggagcgca agtgctggac    1920
aggtggcccg tgtgccccac agggatggct caggggactg tccacctcac ccctgcacct    1980
ctcagcctct gccgccgggc acccccaccc aggctcctgg tgccagatga tgacgacctg    2040
ggtggaaacc taccctgtgg gcacccatgt ccgagccccc tggcatttct gcaatgcaaa    2100
taaagagggt acttttctg ataaaaaaaa aaaaaaaaa aaaaaaaaa aaaaaaaaa        2160 aaaaaaaaaa aaaaaaaaaa aaaaaaa                                       2187
```

INHIBITORS OF REDOX SIGNALING AND METHODS OF USING SAME

RELATED APPLICATION

This application claims continuing status from Provisional Patent Application Serial No. 06/054,566, filed Aug. 1, 1997.

BACKGROUND OF THE INVENTION

1. Field of the Invention

The present invention relates generally to agents which inhibit or interfere with cellular redox systems as well as to the utilization of these agents as diagnostic tools and/or therapeutic agents. More specifically, the present invention relates to agents which interfere with or inhibit a thioredoxin/thioredoxin reductase redox system.

2. Background of the Related Art

Cellular redox systems appear to be very important to normal cellular activity. Cells maintain an intracellular environment that is reducing in the face of a highly oxidizing extracellular environment. Regulated alterations in the intracellular redox state (redox signaling) can modulate events such as DNA synthesis, enzyme activation, selective gene expression, regulation of cell cycle, cell growth, and programmed cell death.

One of the more important consequence of intracellular redox signaling is a change in the oxidative state of select cysteine residues on certain proteins. The post-translational modification of cysteine is difficult to follow since it lacks a convenient marker and is readily reversed when the cell contents are exposed to extracellular oxidizing conditions.

One type of abnormal cell function is abnormal cellular proliferation. Abnormal cellular proliferation is a cardinal feature of human malignancy. During the past decade there has been much insight into the biomolecules that regulate cell proliferation and the pathways in which they operate. These biomolecules have been identified as pharmacological, therapeutic, and/or diagnostic targets for agents which inhibit cellular proliferation.

Another type of abnormal cell function is resistance to apoptosis. Apoptosis is a form of programmed cell death characterized by membrane blebbing, chromatin margination and breakdown of chromosomal DNA into nucleosome-sized fragments. Programmed cell death or apoptosis is an important event in the normal processes of development and tissue remodeling. Loss of apoptosis can lead to diseases associated with cellular proliferation, such as cancer autoimmune disease, inflammation and hyperproliferation disease, while increased apoptosis can lead to neurodegenerative disease and destruction of tissue, as well as cardiovascular damage. Normally, when a cell sustains substantial genetic damage that cannot be repaired by normal DNA repair processes, this is recognized by sensory mechanisms in the cell and a sequence of events is initiated which leads to the death of the cell. Apoptosis results in the death of individual damaged cells and protects the organism from potentially harmful genetic changes that could lead to unregulated cell growth including cancer. Apoptosis resistance has been correlated with induction of the cylcin-dependent kinase inhibitor. There are now documented instances where inhibition of apoptosis by the abnormal expression of an oncogene or the loss of a tumor suppresser genes are closely associated with malignancy. It also appears that as cells develop from a nontransformed state, through a pre-malignant to a fully transformed state, they progressively lose their ability to undergo apoptosis. Apoptosis is also inhibited by some viral infections, in auto immune disease and hyperproliferative skin diseases.

Discovery of molecules which interfere with or inhibit cellular redox systems satisfies a need in the art by providing new diagnostic or therapeutic compositions useful in the detection, prevention, and treatment of diseases related to abnormal cellular activity (i.e., proliferation and apoptosis). These diseases include cancer, viral and other infections, inflammatory diseases, cardiovascular disease, nuerodegenerative diseases, skin disease and immunological disorders.

SUMMARY OF THE INVENTION

Proteins and enzymes involved in the cellular redox reaction provide an attractive site for the development of therapies, diagnostic, and assays for diseased states associated with abnormal cellular function. These agents may serve as chemotherapeutic agents themselves or may increase the efficacy of existing chemotherapeutic agents. Because of the close interactions between intracellular signaling pathways for proliferation and death, effective and selective inhibitors of cell proliferation may also cause desirable cell death.

Strategies for targeting redox related processes in the development of anticancer therapies can be subdivided into three main areas. First, there has been considerable activity in the exploitation of the hypoxic nature of solid tumors. Leading this charge is the search for bio-reductive drugs which will be metabolically activated in the hypoxic fraction. This effort has included the search for agents which will modify (both increase and decrease) the hypoxic fraction. A second approach attempts to alter enzyme levels or activities through gene therapy or induction by non-toxic agents. Finally, cellular signaling pathways having points of redox control have become the target of therapeutic or chemopreventitive intervention. Inhibitors of cellular redox or agents which interfere with cellular redox have strong potential applications as chemopreventative or chemotherapeutic agents.

The present invention is directed to inhibitors of redox signaling and a method of using these inhibitors for therapeutic or prophylactic treatment of a mammalian host caused by abnormal cellular function. The inhibitor(s) may be administered alone or in combination with other therapeutic agents (e.g. other anti-cancer drugs).

This invention relates to a composition comprised of an inhibitor of cellular redox signaling, along with a pharmaceutically acceptable carrier of said inhibitor. It is preferable that the inhibitor(s) of cellular redox signaling also prevent inhibition of apoptosis. Preferably the inhibitor of cellular redox signaling inhibits or interferes with a thioredoxin redox system, and more preferably, the inhibitor of said thioredoxin system is an inhibitor of thioredoxin or an inhibitor of thioredoxin reductase.

The present invention also relates to a composition comprising or including an said inhibitor of cellular redox signaling with an $IC_{50}$ TR/Trx of less than about 50 µg/ml. Preferably the inhibitor of cellular redox signaling has an $IC_{50}$ TR/Trx of less than about 25 µg/ml, more preferably an $IC_{50}$ TR/Trx of less than about 10 µg/ml, even more preferably an $IC_{50}$ TR/Trx of less than about 5 µg/ml, and most preferably the inhibitor of cellular redox signaling has an $IC_{50}$ TR/Trx of less than about 1 µg/ml.

Preferably the inhibitor of cellular redox signaling is selected from the group consisting of NSC 401005, NSC 208731, NSC 382000, NSC 665103, NSC 617145, NSC 618605, NSC 622378, NSC 620109, NSC 163027, NSC 131233, NSC 665102, NSC 631136, NSC 681277, NSC 140377, NSC 603084, NSC 382007, NSC 635002, NSC 620358, NSC 657028, NSC 661221, NSC 622188, NSC 645330, NSC 350629, NSC 102817, NSC 626162, NSC 655897, NSC 267461, NSC 627124, NSC 610187, NSC 624982, NSC 664951, NSC 277293, NSC 608972, NSC 634761, NSC 664271, NSC 665878, NSC 625814, NSC 264054, NSC 652257, NSC 661225, NSC 637828, NSC 647546, NSC 655305, NSC 641396, NSC 668262, NSC 662781 and NSC 626678.

The present invention also relates to a composition comprised of a therapeutically effective amount of an agent which inhibits cellular redox signaling wherein the agent also prevents inhibition of apoptosis. Preferably the agents has an $IC_{50}$ TR/Trx in the range of about 10 µg/ml to about 25 µg/ml, more preferably an $IC_{50}$ TR/Trx in the range of about 5 µg/ml to about 10 µg/ml, even more preferably an $IC_{50}$ TR/Trx in the range of about 1 µg/ml to about 5 µg/ml, and most preferably in a range of about 0.0001 µg/ml to about 1 µg/ml.

The invention also relates to a composition comprised of an inhibitor of cellular redox signaling and a pharmaceutically acceptable carrier, wherein the inhibitor of cellular redox signaling is selected from the group consisting of NSC compounds identified herein and preferably wherein the inhibition is in a therapeutically effective amount.

The therapeutically effective amount is preferably in a range from about 0.05 mg/kg/day to about 5,000 mg/kg/day, more preferably in a range from about 0.5 mg/kg/day to about 500 mg/kg/day, more preferably in a range of about 1 mg/kg/day to about 50 mg/kg/day, and more preferably yet, the therapeutically effective amount is in a range from about 2 mg/kg/day to about 20 mg/kg/day, and most preferably the therapeutically effective amount is in a range from about 5 mg/kg/day to about 10 mg/kg/day.

The invention also relates to a composition for treating a disease comprised of an inhibitor of cellular redox signaling in a dose effective in treating said disease. The disease is preferably related to redox function and more preferably related to abnormal cellular proliferation and/or abnormal apoptosis. The disease is preferably selected from the group consisting of cancer, reperfusion injury following ischemia, hepatitis, amyetrophic lateral sclerosis, neurodegenerative diseases, Alzheimers diseases Autoimmune disease, Sjogren's syndrome, Lupus, rheumatoid arthritis, HIV, Hermansky-Pudlack syndrome, retinal oxidative damage, retinopathy, skin hyperplasia, aging, ultraviolet damage, wound healing, Crohns' disease, ulcerative colitis, angiogenesis, uterine disorders, adult respiratory distress syndrome (ARDS), lung disorders, viral and other infections such as herpes virus, pox virus and adenovirus infections, inflammatory conditions, automimmune diseases such as, systemic lupus erythematosus, rhematoid arthritis, psoriasis, inflammatory bowel disease and autoimmune diabetes, immune mediated glomerular nephritis, hyperproliferative diseases such as fibrosis, psoriasis and mycosis fungoides. It is preferable that the inhibitor of cellular redox signaling inhibits thioredoxin activity which is associated with thioredoxin and thioredoxin reductase.

This invention also relates to a method of inhibiting growth in a cell comprised of contacting the cell with an effective amount of an inhibitor of redox activity, wherein the inhibitor of redox activity is an inhibitor of a thioredoxin/ thioredoxin reductase redox system, and even more preferably wherein said agent prevents inhibition of apoptosis. It is preferable that the inhibitor of cellular redox signaling has an $IC_{50}$ TR/Trx of less than about 50 µg/ml, preferably less than about 25 µg/ml, more preferably less than about 10 µg/ml, even more preferably an $IC_{50}$ TR/Trx of less than about 5 µg/ml, and most preferably the inhibitor of cellular redox signaling has an $IC_{50}$ TR/Trx of less than about 1 µg/ml. Preferably, the inhibitor of cellular redox signaling is selected from the group of NSC compounds referred to herein.

The growth in a cell is inhibited with an effective amount of inhibitor which may be based on the effectiveness of previously identified active inhibitors. Preferably, the therapeutically effective amount is in a range from about 0.01 mg/kg/day to about 500 mg/kg/day. More preferably said therapeutically effective amount is in a range from about 0.1 mg/kg/day to about 250 mg/kg/day. Even more preferably said therapeutically effective amount is in a range from about 1 mg/kg/day to about 50 mg(kg/day. More preferably yet, said therapeutically effective amount is in a range from about 1 mg/kg/day to about 20 mg/kg/day, and most preferably said therapeutically effective amount is in a range from about 1 mg/kg/day to about 10 mg/kg/day.

Another aspect of the present invention is a method of inhibiting tumor growth comprised of administering an effective amount of an inhibitor of thioredoxin activity to a patient in need thereof. Preferably, but certainly not a requirement, is that the agent also prevents inhibition of apoptosis. The method of inhibiting tumor growth involves administering the inhibitor in the therapeutically effective amounts described above.

Finally, the present invention relates to a method of treating a diseased state comprised of administering a therapeutically effective amount of an agent which inhibits thioredoxin activity wherein said agent has a predetermined acceptable $IC_{50}$ TR/Trx as described above.

BRIEF DESCRIPTION OF THE DRAWINGS

The features, aspects and advantages of the present invention will become better understood with regard to the following description, appended claims, and accompanying drawings where:

DETAILED DESCRIPTION OF THE INVENTION

Figure 1:
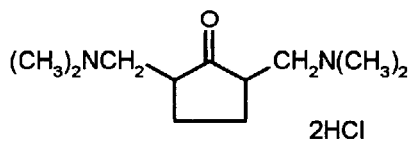
FIG. 1 illustrates the structures of inhibitors of the thioredoxin redox system with $IC_{50}$ values of about 0.39 to less than about 1.0 µg/ml (NSC 131233, NSC 665102, NSC 631136, NSC 140377 and NSC 603084).
Figure 1:
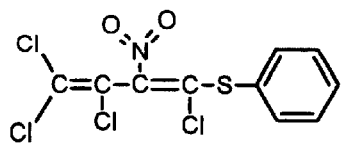
Figure 1:
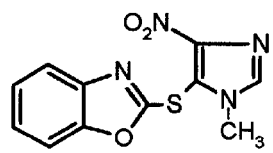
Figure 1:
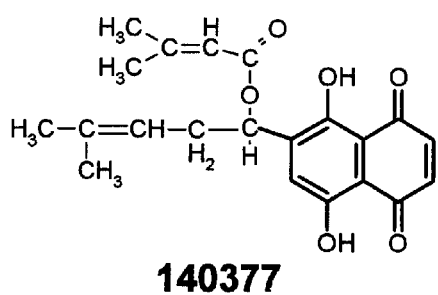
Figure 1:
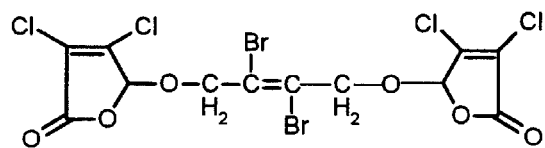
Figure 2:
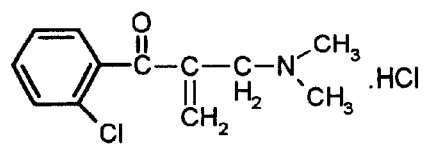
FIG. 2 illustrates the structures of inhibitors of the thioredoxin redox system with $IC_{50}$ values of about 1.1 to less than about 2.0 µg/ml (NSC 382007, NSC 635002, NSC 620358, NSC 657028, NSC 661221 and NSC 622188).
Figure 2:
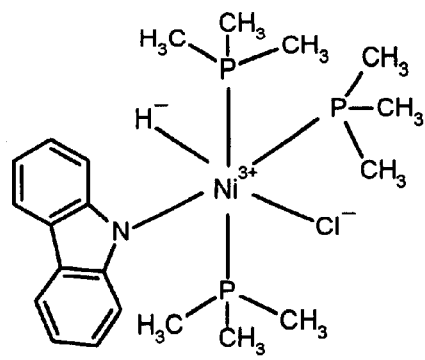
Figure 2:
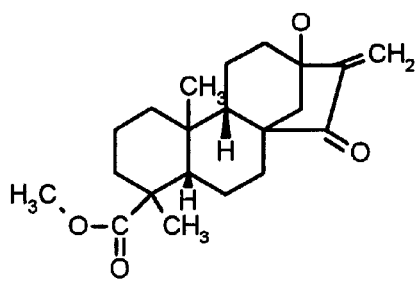
Figure 2:
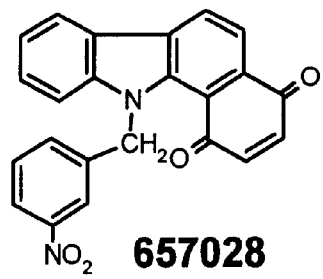
Figure 2:
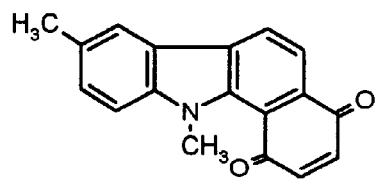
Figure 2:
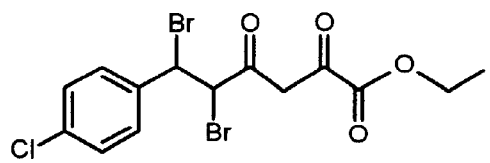
Figure 3:
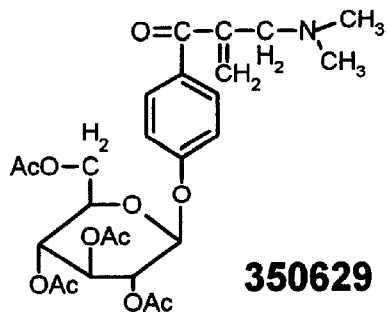
FIG. 3 illustrates the structures of inhibitors of the thioredoxin redox system with $IC_{50}$ values of about 2.0 to about 4.0 µg/ml (NSC 350629, NSC 102817, NSC 626162, NSC 655897, NSC 267461, NSC 627124, NSC 610187 and NSC 624982).
Figure 3:
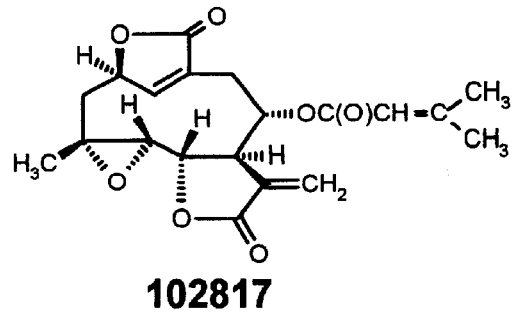
Figure 3:
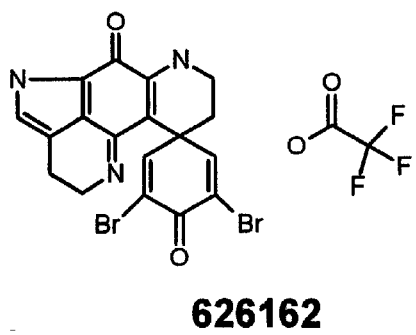
Figure 3:
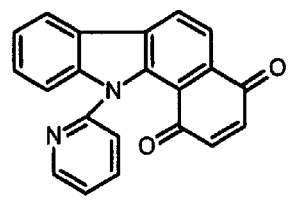
Figure 3:
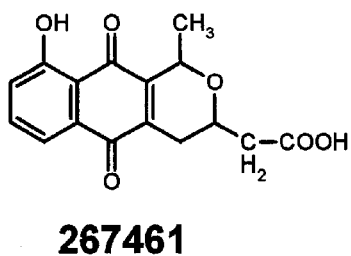
Figure 3:
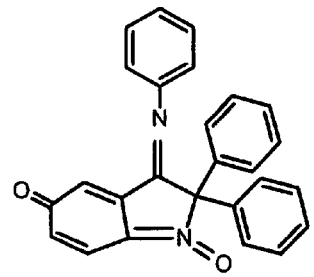
Figure 3:
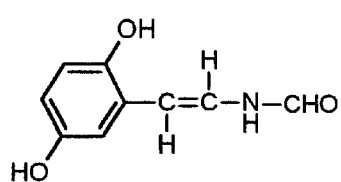
Figure 3:
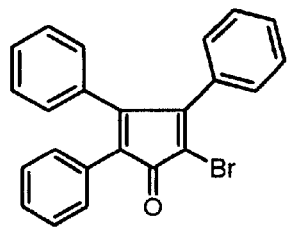
Figure 4:
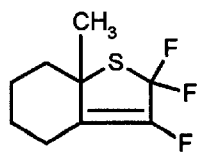
FIG. 4 illustrates the structures of inhibitors of the thioredoxin redox system with $IC_{50}$ values of about 6.7 to about 10.0 µg/ml (NSC 664951, NSC 277293, NSC 608972, NSC 634761, NSC 664271 and NSC 665878).
Figure 4:
Figure 4:
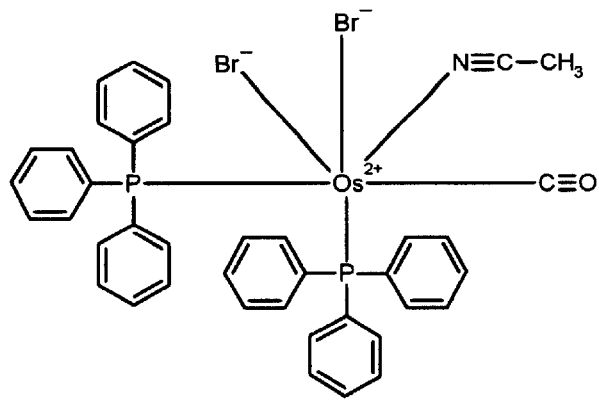
Figure 4:
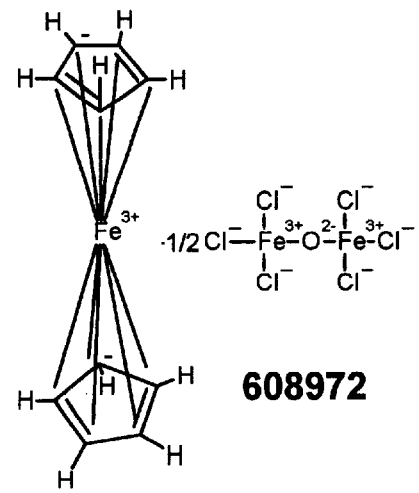
Figure 4:
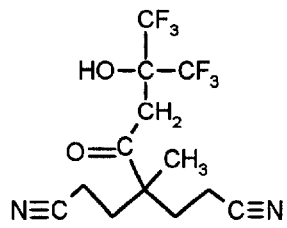
Figure 4:
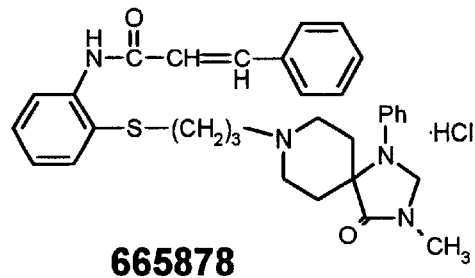
Figure 5:
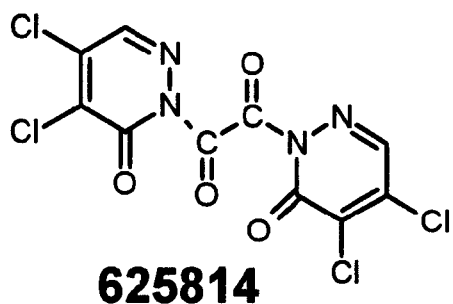
FIG. 5 illustrates the structures of inhibitors of the thioredoxin redox system with $IC_{50}$ values of about 11.0 to about 25.0 µg/ml (NSC 625814, NSC 264054, NSC 652257, NSC 661225, NSC 637828 and NSC 647546).
Figure 5:
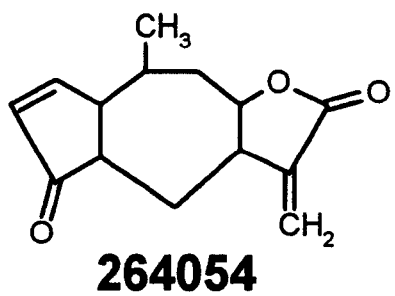
Figure 5:
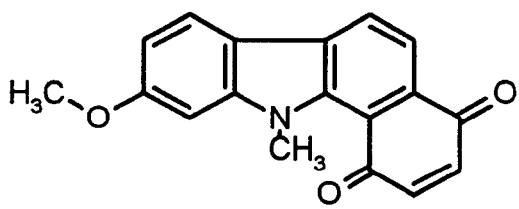
Figure 5:
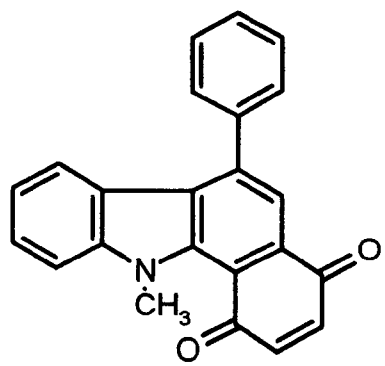
Figure 5:
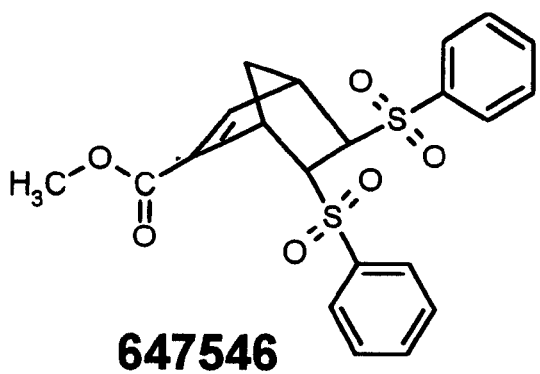
Figure 5:
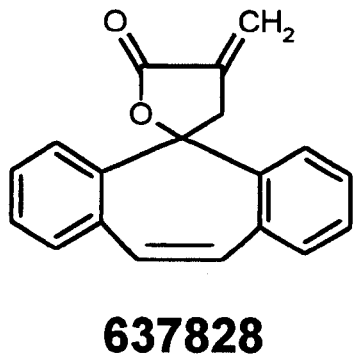
Figure 6:
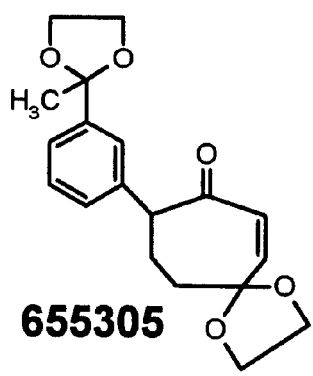
FIG. 6 illustrates the structures of inhibitors of the thioredoxin redox system with IC5o values of about 33.0 to about 50.0 µg/ml (NSC 655305, NSC 641396, NSC 668262, NSC 662781, and NSC 626678).
Figure 6:
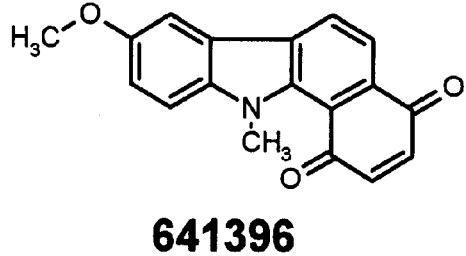
Figure 6:
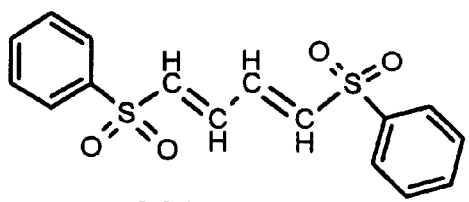
Figure 6:
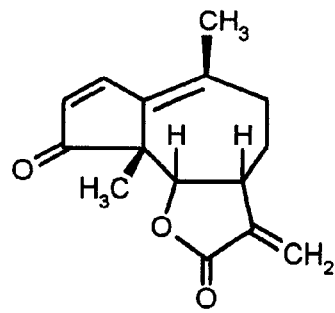
Figure 6:
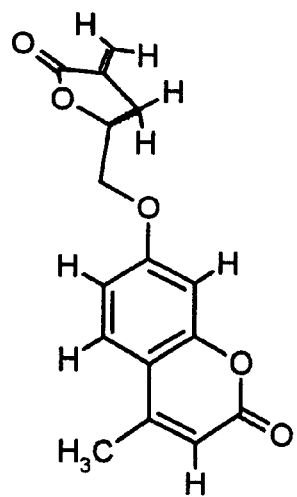

The present invention relates to compounds or mixtures of compounds which interfere, inhibit, or compete with redox systems, particularly redox systems involving proteins having cysteine residues, and more particularly to redox systems involving thioredoxin and/or thioredoxin reductase. The agents may be used alone or in combination with other thereapeutic agents or therapeutic methods.

Combination therapy (i.e., chemotherapy) using two or more therapeutic drugs to treat malignant tumors in humans is currently in use in research and in the clinic and is specifically contemplated herein. For cancer, the therapeutic or anti-cancer drugs may be antimentabolites, alkylating agents, antibiotics, general poisons, etc. Combinations of drugs are administered in an attempt to obtain a synergistic cytotoxic effect on most cancers, e.g., carcinomas, melanomas, lymphomas and sarcomas, and to reduce or eliminate emergence of drug-resistant cells and to reduce side effects to each drug.

As used herein, the term "prophylactic or therapeutic" treatment refers to the administration to the host or subject of inhibitors of redox signaling either before or after onset of the biological damage to the host. If the inhibitor or biological agent(s) are administered prior to exposure to the agent causing the biological damage or to prevent occurance of the disease, the treatment is prophylactic (i.e., it protects the host against the damage), whereas if it is administered after exposure to the agent causing the damage, the treatment is therapeutic (i.e., it alleviates the existing damage).

As used herein, the term "about" means plus or minus 10% of the number to which reference is being made. For example, about 10 grams means in the range of 9–11 grams.

As used herein, $IC_{50}$ refers to the concentration causing 50% inhibition in activity in the system being measured. For example, in the TR/Trx insulin reduction assay, $IC_{50}$ is defined as that concentration of inhibitor which causes a 50% decrease in the reduction of insulin by TR/Trx. When referring to the particular system being analyzed $IC_{50}$ is typically followed by an abbreviation referring to that system (i.e., $IC_{50}$ TR/Trx for the above described thioredoxin redox system which is comprised of thioredoxin reductase and thioredoxin).

As used herein, $GI_{50}$ refers to that concentration of inhibitor which produces a mean 50% growth inhibition. Similar to the $IC_{50}$, $GI_{50}$ normally designated the system being analyzed or the type of cell lines. For example $GI_{50}$ (all tumors) as used herein refers to the mean growth inhibition in all 60 cell lines of the National Cancer Institute, while $GI_{50}$ (leukemias) refers to a mean 50% growth inhibitor for the leukemia cell line.

The pharmaceutical compositions utilized in this invention may be administered by any number of routes including but not limited to, oral, intravenous, intramuscular, intraarterial, intramedullary, intrathecal, intraventricular, transdermal, subcutaneous, intraperitoneal, intanasal, enteral, topical, sublingual, or rectal means. In addition to the active ingredients, these pharmaceutical compositions may contain suitable pharmaceutically-acceptable carriers comprising excipients and auxiliaries which facilitate processing of the active compounds into preparations which can be used pharmaceutically.

As used herein, the term "pharmaceutically acceptable carrier" refers to a carrier medium which does not interfere with the effectiveness of the biological activity of the active ingredients and which is not toxic to the hosts to which it is administered.

As used herein, the term "pharmacologically effective amounts" as applied to inhibitors of redox signaling refers to the amount of each component in the mixture or administered to the host that results in an increase in the therapeutic index of the host. The "therapeutic index" is defined for purposes herein in terms of efficacy (extent of tumor or infection reduction or other cure) and/or in terms of toxicity to the host. For non-human hosts, if the efficacy increases at least 50% over the efficacy using an excipient control (e.g., phosphate buffered saline) and the ratio of mean body weight at the end of the evaluation period for efficacy response to mean body weight at the start of treatment is at least 0.90 (i.e., no greater than 10% body weight loss), the therapeutic index has increased. The ratio of mean body weights indicates the extent of toxicity, with a value of 1 indicating no toxicity. For non-human hosts being treated for cancer, the extent of efficacy achieved may be measured by the ratio of mean tumor volume at the end of the evaluation period for efficacy response to mean tumor volume at the start of treatment. A reduction in the ratio of at least 50% of treated over excipient control indicates increased efficacy. The most preferred doses, schedules, and types of thereapeutic agents are those that achieve a mean tumor volume ratio of between 0 and 5, with a value of 0 being optimum and indicating a cure. For human hosts, if the efficacy increases at least 50% upon treatment with the thereapeutic agents and the toxicity is acceptable, i.e., no more than fever, chills, and/or general malaise, the therapeutic index has increased. For human hosts being treated for cancer, the extent of efficacy is generally ascertained in the clinic by measuring the perpendicular diameters of the products of all measured disease. For cancer, the treatment is not considered therapeutic if after treatment, or if an existing tumor burden is not eliminated or decreased. The effect of the doses may diminish with time. For humans the dose may be repeated for months or even years.

A therapeutically effective dose refers to that amount of active ingredient, for example, NSC compound, which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The thereapeutic index can be defined dose ration between therapeutic and toxic effects (the ratio $LC_{50}/ED_{50}$). Pharmaceutical compositions which exhibit large therapeutic indices are preferred.

As used herein, the term "biological damage to the host caused by abnormal cellular redox" refers to any damage to cellular, tissue or other body parts or functions sustained by the host as a result of abnormal redox in the host (i.e. abnormal cellular proliferation).

The term "cancer" as used in the above definition refers to any neoplastic disorder, including such cellular disorders as, for example, renal cell cancer, Kaposi's sarcoma, chronic leukemia, breast cancer, sarcoma, ovarian carcinoma, rectal cancer, prostate cancer, throat cancer, melanoma, colon cancer, bladder cancer, mastocytoma, lung cancer and gastrointestinal or stomach cancer. Preferably, the cancer is colon cancer, melanoma, renal cell cancer, sarcoma, lung cancer, adenocarcinoma, prostate or breast cancer.

The thioredoxin redox couple (TR/Trx) is a ubiquitous redox system found in both prokaryotic and euktryotic cells. The thioredoxin system is comprised primarily of two elements: thioredoxin and thioredoxin reductase. Thioredoxin reductase is a NADPH-dependent selenium containing flavoprotein that catalyzes the reduction of thioredoxin.

E. coli thioredoxin reductase is a 70 kDa homodimer. The active site cysteine residues, Cys-135 and Cys-138, receive electrons from FADH2 and transfer them to the active cysteine bond of thioredoxin. During reduction, thioredoxin reductase undergoes a conformation change which protects the reduced active site cysteines from the aqueous phase, preventing spontaneous oxidation. Upon binding of oxidized thioredoxin to the active site, thioredoxin reductase undergoing a conformation change to expose the active site cysteines, allowing reduction of thioredoxin's cystine bond. Thioredoxin reductase of higher organisms is a 116–129 kDa homodimer. Human placental thioredoxin reductase has been cloned. The active site of human thioredoxin reductase has a conserved Cys-Val-Asn-Val-Gly-Cys amino acid sequence in the FAD binding domain and, unexpectedly, a C-terminal Gly-Cys-CysSe-Gly amino acid sequence due to the normal DNA stop codon TGA coding for selenocysteine (CysSe) because of a 3'-untranslated signal stem loop signal sequence. The CysSe residue is critical for the activity of human thioredoxin reductase. Studies have shown that it can reduce bacterial thioredoxin, although at a decreased rate compared to human thioredoxin reductase A gene for human thioredoxin reductase is located at chromosomal position 12q23-q24.1.

Thioredoxins are a class of low molecular weight redox proteins characterized by a highly conserved -Cys-Gly-Pro-Cys-Lys active site. The cysteine residues at the active site of thioredoxin undergo reversible oxidation-reduction catalyzed by thioredoxin reductase. The human thioredoxin gene has been mapped to 9q31. Analysis of genomic clones of thioredoxin have found that the entire gene spans 13 kb and is comprised of 5 exons. X-ray crystal studies have identified a highly conserved 12 amino acid hydrophobic surface on vertebrate, but not bacterial thioredoxins, accounting for 10% of the solvent accessible surface of the protein.

Human thioredoxin has been cloned and sequenced. It has been shown that the deduced amino acid sequence of thioredoxin is identical to that of a previously known protein called eosinophil cytotoxicity stimulating factor or adult T-cell leukemia-derived factor (ADF). A human mitochondrial thioredoxin has also been identified and a complete mRNA sequence was filed with GeneBank (Miranda-Vizuete A et al. HSU78678 submitted Nov. 18, 1996. Uni-Gene hs. 79366).

Human thioredoxin has a 27% amino acid identity to E. coli thioredoxin and contains in addition to the catalytic site cysteine residues other cysteine residues that are not found in bacterial thioredoxin. As discussed below, very high levels of thioredoxin have been seen in some human tumor cell lines and primary human tumors. These cysteine residues appear to give human thioredoxin unique growth promoting activity.

Mutagenesis studies characterizing thioredoxin's conserved active site sequence have been reported. Conversion of $Cys^{32}$ and $Cys^{35}$ to Serine residues, either singly or together, results in a loss of the ability of the protein to be reduced by thioredoxin reductase and results in a loss of thioredoxin growth stimulating and antiapoptosic activity. A residue that has drawn particular attention is a highly conserved lysine group adjacent to the C-terminal-most active-site cysteine. The presence of the positively charged amine group so close to the active site has led to the suggestion that it is critical in maintaining the thiolate anion of Cys-32. However, the highly conserved lysine group adjacent to the active site does not appear to be essential for the reduction of either prokaryotic or eukaryotic thioredoxin by thioredoxin reductase, but is seemingly required for optimizing protein interactions with the flavoenzyme as evidenced by the increase in the Km values for the mutant Lys-36 human thioredoxin.

Thioredoxin exerts specific redox control over a number of transcription factors to modulate their DNA binding and, thus, to regulate gene transcription. Transcription factors regulated by thioredoxin include NF-kB, TFIIIC, BZLF1 and the glucocorticoid receptor. The transcription factor activator protein-1 (AP-1) (Fos/Jun heterodimer) is subject to redox control by the nuclear redox factor Ref-1/HAP-1 which, in turn, is reduced by thioredoxin. The importance of redox regulation of transcription factor activity is illustrated by the oncogene v-fos where a point mutation converts $Cys^{154}$ to a serine residue resulting in constitutive activation and DNA binding of the Jun protein.

Human recombinant thioredoxin has been shown to stimulate the proliferation of human epithelial cancer cells. This appears to be due to thioredoxin's ability to enhance the activity of endogenously produced growth factors, either by acting on the factors themselves or affecting the factors' interaction with its cell surface receptor. For example, thioredoxin at nanomolar levels produces a $10^3$ fold enhancement of the growth stimulating activity of interleukin-2 and a $10^2$ fold enhancement of the activity of basic-fibroblast growth factor with MCF-7 human breast cancer cells. Mutant redox-inactive forms of thioredoxin lacking the active site cysteine residues and E. coli thioredoxin are devoid of growth stimulating activity.

It has been found that exogenously added thioredoxin stimulates mouse fibroblasts and a number of human solid tumor cells lines.

Thioredoxin stimulates cell growth up to 90% as effectively as 10% fetal bovine serum stimulation. This is a characteristic exhibited by few other growth factors. One exception to this appears to be HepG2 cells whose proliferation is stimulated by thioredoxin in serum free medium but is inhibited in the presence of 0.5% serum.

Mechanistically, thioredoxin does not appear to stimulate cell growth along classical lines by acting on a specific cell-surface receptor. There was no evidence for saturable binding of $^{125}$I-thioredoxin to the surface of MCF-7 breast cancer cells and there was minimal uptake of the $^{125}$I-thioredoxin into the cells. Instead, thioredoxin appears to exert its cell growth stimulating effect by sensitizing cells to growth factors produced by the cell itself. Replacing medium each day with fresh medium and thioredoxin reductase completely abolishes the increase in cell proliferation. Such a process presumably removes the factors secreted by cells that are necessary for thioredoxin-induced cell growth. There was a significant correlation between the ability of a number of human cancer cell lines to proliferate in the absence of serum, which is presumably due to the autocrine production of growth factors by the cell, and the extent of stimulation by thioredoxin. This helper, or voitocrine, mechanism appears to be unique to thioredoxin and requires the redox active form of the protein, in addition to other features present in human thioredoxin but absent in E. coli thioredoxin.

The $EC_{50}$ for thioredoxin growth stimulation in MCF-7 breast cancer cells is 350 nM which is considerably higher than the 4–18 nM concentration of thioredoxin found in serum. Higher thioredoxin concentrations exist in tissues, 1 to 10 $\mu$M, which if released extracellularly might stimulate cell proliferation. Thioredoxin protein levels are elevated in a variety of human primary tumors including human cervical neoplastic squamous epithelial cells, gastric carcinoma, and hepatocellular carcinoma. It has been found that a significant number of human primary lung and colon cancers have increased thioredoxin mRNA compared to paired normal tissue. In human primary gastric carcinoma increased levels of thioredoxin are associated with aggressive tumor growth measured by high levels of proliferation antigen and low levels of apoptosis. NIH 3T3 cells stably transfected with thioredoxin cDNA show an increase in growth rate, while MCF-7 breast cancer cells transfected with cDNA for the redox inactive C32S/C35S mutant thioredoxin will no longer form colonies in soft agar. These results suggest that increased thioredoxin gene expression could contribute, in part, to the increased growth rate and transformed phenotype of some human tumors.

Molecular proof that thioredoxin reductase and thioredoxin offer rational target for the development of drugs to treat human cancer comes from studies where mouse NIH 3T3 cells and MCF-7 human breast cancer cells have been stably transfected with cDNA for wild-type human thioredoxin or the redox-inactive mutant thioredoxin. NIH 3T3 cells transfected with wild type thioredoxin achieve increased cell saturation densities on plastic surfaces. Thioredoxin transfected MCF-7 human breast cancer cells showed unaltered proliferation on plastic surfaces but a 4-fold increased colony formation in soft agar. Anchorage independent growth in agar is a characteristic of a transformed nonhematological cells. Stable transfection of NIH 3T3 and MCF-7 cells with a redox-inactive mutant thioredoxin, resulted in inhibition of the growth on plastic surfaces, and >70% inhibition of colony formation in agar by MCF-7 cells. When inoculated into immunodeficient mice the thioredoxin transfected MCF-7 cells formed tumors, as did the vector-alone transfected cells, but tumor formation by redox-inactive thioredoxin transfected MCF-7 cells was completely inhibited.

Thioredoxin has been identified as a component in the early pregnancy factor (EPF) system, a complex array of factors present in the sera of pregnant mammals. The binding of lymphocytes to red blood cells, i.e., rosette bud formation, by EPF occurs during the initial onset of pregnancy and several proteins of the EPF complex may act synergistically, or in combination. A mutagenesis study of human thioredoxin showed that the redox active, catalytic site Cys-32 and Cys-35 residues were not essential for this function, but that Cys-74 was.

In addition to its involvement in cellular proliferation, the TR/Trx system also appears to be involved or associated with apoptosis. Apoptosis or programmed cell death has also been associated with normal cellular behavior. There is now considerable evidence that an increase in reactive oxygen species constitutes an intracellular signal that can lead to apoptosis. Apoptosis can be induced in a number of cell systems by $H_2O_2$, reactive oxygen species generated by the redox cycling of quinones and radiation. It appears that c-myc, which is essential for apoptosis in many systems, is induced by $H_2O_2$ and reactive oxygen species. Hypoxia and antioxidants inhibit apoptosis induced by these treatments. Thioredoxin protects lymphoma cells against TNF-α-mediated cell killing. The survival of embryonic mouse neurons is enhanced by thioredoxin, as well as by 2-mercaptoethanol and N-acetylcysteine. In the same studies, U251 astrocytoma cells were seen to produce increased levels of thioredoxin in response to $H_2O_2$ treatment. Elevated thioredoxin levels have also been observed in glial cells of the gerbil brain during reperfusion after ischaemia. Thus, thioredoxin secreted by glial cells may protect neurons, in vivo, from oxidative stress-induced cell death.

A model of apoptosis where oxidant signaling appears to play a major role is steroid hormone-induced apoptosis of the murine thymoma-derived WEHI7.2 cell. Studies have shown that during dexamethasone-induced apoptosis there is a selective decrease in the transcript levels of a number of antioxidant defense enzymes, including both Mn and Cu/Zn superoxide dismutases, catalase, glutathione peroxidase, thioredoxin, and DT-diaphorase. The changes in antioxidant enzyme transcript levels are first seen 8 hr after dexamethasone treatment and precede apoptosis which is apparent by 24 hr and maximal by 48 hr. The superoxide dismutase, catalase and DT-diaphorase activities of dexamethasone-treated WEHI7.2 cells shows a fall by 24 hr and is maximally depressed by 48 hr. It appears that bcl-2 is able to prevent a decrease in antioxidant defense enzyme levels despite a decrease in gene transcription caused by dexamethasone treatment. This might be related to the inhibition by bcl-2 of proteases of the ICE family which might be able to degrade the antioxidant enzymes. Treatment of WEHI7 2 cells with the antioxidants trolox (a water soluble vitamin E derivative), catalase and selenium, as well as hypoxic conditions, prevent dexamethasone-induced apoptosis. This provides evidence that the decrease in antioxidant enzymes could lead to an increase in cellular reactive oxygen species responsible for signaling apoptosis.

Transfection of WEHI7.2 lymphoid cancer cells with thioredoxin cDNA blocks apoptosis induced by a variety of agents, including, etoposide, staurosporine, thapsigargin and glucocorticoids, which is similar to the pattern seen with the antiapoptotic oncogene bcl-2. When inoculated into scid mice, the trx transfected cells form tumors that grow faster than wild type or bcl-2 transfected WEHI7.2 cell tumors, due to a decreased spontaneous rate of apoptosis, and that are resistant to growth inhibition by treatment with dexamethasone.

In addition to its growth enhancing effects thioredoxin appears to cause tumors to be resistant to anticancer drugs. Thus, thioredoxin appears to be a complete and potent cancer causing gene that plays an important role in human cancer.

Many diseases appear to be associated with weakened antioxidant defenses and oxidative stress. It should be emphasized that the increase in reactive oxygen species that follows a decrease in antioxidant enzymes is, most likely, a signaling event and not an effector mechanism for apoptosis. That is, oxygen radicals are not directly responsible for the DNA degradation and membrane damage seen during the final common pathway of apoptosis as has been proposed by some investigators. Furthermore, reactive oxygen species are probably only one of a number of signaling events that can initiate apoptosis. It is known, for example, that hypoxia does not inhibit apoptosis caused by staurosporine, a non-specific PKC inhibitor, by the FAS receptor, by withdrawal of IL-3 from IL-3-dependent cells or by the topoisomerase inhibitor camptothecin. The endogenous formation of reactive oxygen species could however, be a constitutive factor that tends to drive cells to apoptosis even in the absence of exogenous stimuli. Such a model of apoptosis is consistent with the view that the default state of cells is to die by programmed cell death unless kept alive by specific signals from other cells provided by growth factors and anti-apoptotic agents. It may be that cancerous cells deliver their own survival signals, thus, becoming resistant to both intrinsic and induced apoptosis.

There are other disease states where weakened antioxidant defenses and oxidant stress are associated with inappropriate cell death. Genetic studies of individuals with amylotrophic lateral sclerosis have identified mutations in the gene coding for Cu,ZnSOD. These mutations result in decreased enzyme activity, which may contribute to the observed pathology of motor neuron death. CD4+ cells and lymph nodes from AIDS patients have decreased levels of GSH and thioredoxin, respectively. Catalase, MnSOD and glutathione peroxidase activities drop in T cell lines grown in vitro, after infection with the HIV virus. α-amyloid is a neurotoxic peptide that aggregates in the brain of Alzheimer's patients and has been found to generate free radical peptides. This has led to the hypothesis that oxidative stress, specifically, membrane damage mediated by the α-amyloid-derived radicals, leads to the neurodegeneration seen with Alzheimer's disease. Two apoptosis-linked genes have been isolated were able to inhibit T cell receptor-induced cell death. ALG-2 which codes for a $Ca^{2+}$-binding protein may regulate signals along the death pathway, and ALG-3, a partial complementary DNA that is homologous to the familial Alzheimer's disease gene STM2, may link that cell death pathway to Alzheimer's disease.

Thioredoxin mRNA is increased, in some cases up to 100-fold compared to corresponding normal tissue, in almost half human primary lung, colon and gastric tumors examined. Thioredoxin levels have also been reported to be increased in human cervical neoplastic squamous epithelial cells and hepatocellular carcinoma. Thioredoxin activity is increased almost two-fold in human colon cancer compared to normal colonic mucosa. Thioredoxin is known to be excreted from cells by a leaderless secretory pathway so that overexpression of thioredoxin could lead to production of an autocrine growth factor for some human cancers.

We have recently identified two new human thioredoxin reductases. These human reductases appear to be tissue specific and have specific cellular distribution patterns. Sequence data is supplied herein as SEQUENCE 1 and SEQUENCE 2.

The thioredoxin redox system appears to play an important role in a number of diseased states, specifically maintaining the transformed phenotype of some human cancers. These data illustrate that thioredoxin over-expression causes cell transformation, aggressive tumor growth and resistance to spontaneous and drug induced apoptosis and thus is a rational target for cancer drug development. There is a need for drugs which will inhibit the activity of the thioredoxin system and consequently decrease tumor cell growth and prevent aggressive cancer disease. Inhibitors of thioredoxin and/or thioredoxin reductase appear to achieve this goal. The ability to alter cellular redox in such a fashion as to manipulate the growth regulating proteins offers a particularly intriguing possibility for novel anticancer drug development.

Over-expression or under-expression of either thioredoxin reductase or thioredoxin appear to play a role in the development of disease. Increased expression of thioredoxin is associated with increased growth leukemia and lymphoma cells, autoimmune disease such as Sjogren's syndrom, rheumatoid arthritis, Lupus, cancer and AIDS. A deficiency of thioredoxin reductase is associated with Hermansky-Pudlack syndrome. Other redox associated diseases include, atherosclerosis, diabetic complications, retinopathies, angiogenesis, Amyetrophic lateral sclerosis and other neurodegenerative disease, arthritis, skin disease (aging and ultraviolet damage), wound healing, liver disease, Wilson's disease, Crohns' disease, ulcerative colitis, uterine disorders, Adult respiratory distress syndrom (ARDS), lung disorders, reperfusion injury following ischemia (eg. cardiomyopathy, stroke) viral and other infections such as herpes virus, pox virus and adenovirus infections, inflammatory conditions, automimmune diseases such as systemic lupus erythematosus, rhematoid arthritis, psoriasis, inflammatory bowel disease and autoimmune diabetes, immune mediated glomerular nephritis, hyperproliferative diseases such as fibrosis, psoriasis and mycosis fungoides.

As an initial approach to developing agents which might selectively inhibit thioredoxin-dependent cell proliferation and/or apoptosis we studied a series of imidazolyl disulfides, typical of which is 1-methylpropyl 2-imidazolyl disulfide (IV-2). Prolonged incubation of thioredoxin with the alkyl 2-imidazolyl disulfide results in irreversible inhibition of the thioredoxin as a substrate for reduction by thioredoxin reductase. The inhibition appears to be specific for Cys 73 of thioredoxin, which remains a substrate for thioredoxin. In culture, IV-2 shows greater inhibition of thioredoxin than serum-dependent cell proliferation, suggesting that it may be producing its effect by inhibiting the thioredoxin redox system.

Cell Screen: The compounds IV-2 and DLK-36 (benzyl-2-imidazolyl disulfide) another preferred disulfide are shown below:

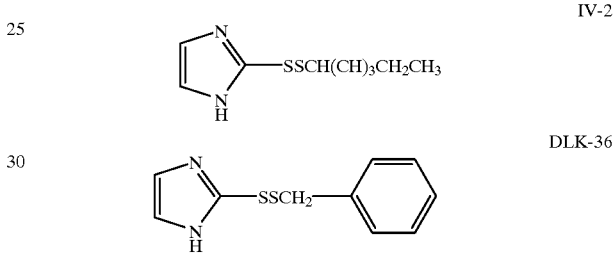

IV-2 has also been shown to exhibit dose-dependent antitumor activity against human MCF-7 breast cancer and HL-60 xenografts growing in scid mice. IV-2 and the second disulfide, DLK-36, produced responses of seen 98% and 65% tumor inhibition respectively against the MCF-7 tumor system. IV-2 and DLK-36 showed antitumor activity against HL-60 leukemia growing in scid mice with a number of the animals without tumor at day 45 for each compounds.

The min (multiple intestinal neoplasia) mouse has been used herein, to test for chemopreventive activity of IV-2. The min mouse has a germline mutation in the APC gene seen in human familial adenomatous polyposis (FAP). This model was chosen because of its genetic basis and as an alternative to chemically-induced models of colon cancer. The majority of the tumors that develops in the adult min mice are in the small intestine, although tumors are first diagnosed in the colon. FAP represents a high risk group of subjects with a readily identifiable early end-point marker that is suitable for trials of novel chemopreventive agents. Compound IV-2 in the diet at 250 ppm (a dose less than optimal due to limited supply) reduced the number of tumors in the colon by 70% (p=0.0160) and caused a significant reduction in the size of remaining tumors (p<0.001 compared to control).

Beyond the therapeutic activity of thioredoxin reductase and thioredoxin and inhibitors thereof, new classes of inhibitors of both thioredoxin reductase and thioredoxin would be useful both as novel pharmacological probes for studying the roles of these enzymes in signal transduction pathways and as leads for structure optimization and structure/activity studies. Data from the National Cancer Institute's (NCI's) panel of 60 human cancer cell lines (as described by Monks et al., Feasibility of a high-flux anticancer drug screen using a diverse panel of cultured human tumor cell lines. *Journal of the National Cancer Institute*, 83, 757, (1991), which is hereby incorporated by reference for its teaching relating to screening) was analyzed using the COMPARE pattern recognition program (as described by Paull et al., Display and analysis of patterns of differential activity of drugs against human tumor cell lines: development of mean graph and COMPARE algorithm. *Journal of the National Cancer Institute*, 81, 1088, (1989), which is hereby incorporated by reference for its teaching relating to the COMPARE algorithm) with the two disulfide drugs (IV-2 and DLK-36) as seed compounds in order to identify other compounds with similar patterns of growth inhibition or as inhibitors of the thioredoxin redox system.

The preselection of molecules using the COMPARE analysis allow us to pursue molecular targets knowing in advance the growth inhibitory effects of the compounds and accordingly, reduces the number of compounds that must be tested from among over 50,000 compounds already screened in the NCI investigational drug data base. Using this cell directed screening approach (CDSA) we have identified a number of inhibitors of the thioredoxin redox system with a hit rate in the primary screen of 77% for compounds with $IC_{50}s \leq 10$ μg/ml compared to a hit rate of 3 to 10% by screening of non-related or randomly selected natural products.

The materials and methods of the present invention are as follows: Enzymes: Thioredoxin reductase, specific activity 43.6 μmole NADPH reduced/min/mg protein at 21° C., was purified from human placenta as previously described (Oblong et al., 1993) Glutathione reductase, specific activity 141.2 μmole NADPH reduced/min/mg protein at 21° C., was purified from aged human red blood cells (Colmon & Black, 1965). Human recombinant thioredoxin was expressed in *E. coli* and purified as previously described (Gasdaska et al., 1994). The thioredoxin was stored at −20° C. with 5 mM dithiothreitol which was removed before use with a desalting column (PD10, Pharmacia, Uppsala, Sweden).

Assays: Microtitre plate colorimetric assays, based on the increase in absorbance at 405 nM which occurs as dithionitrobenzoic acid (DTNB) is reduced by the enzyme-mediated transfer of reducing equivalents from NADPH, were developed for thioredoxin reductase, thioredoxin reductase/thioredoxin-dependent insulin-reduction and glutathione reductase. Thioredoxin reductase/thioredoxin-dependent insulin reducing activity was measured in an incubation with a final volume of 60 μl containing 100 mM HEPES buffer, pH 7.2, 5 mM EDTA (HE buffer), 1 mM NADPH, 1.0 μM thioredoxin reductase, 0.8 μM thioredoxin and 2.5 mg/ml bovine insulin. Incubations were for 30 min at 37° C. in flat-bottom 96 well microtitre plates. The reaction was stopped by the addition of 100 μl 6 M guanidine HCl, 50 mM Tris pH 8.0, and 10 mM DTNB and the absorbance measured at 405 nM.

Assays of thioredoxin reductase or glutathione reductase were run in flat bottom 96-well microtitre plates thioredoxin reductase activity was measured in a final incubation volume of 60 μl containing HE buffer, 10 mM DTNB, 1.0 μM thioredoxin reductase and 1 mM NADPH. Glutathione reductase activity was measured in a similar assay in which thioredoxin reductase was replaced by 1.0 μM glutathione reductase. Compounds were diluted in HE buffer and added to the wells as a 20 μl aliquot, and thioredoxin reductase or glutathione reductase were then added also as a 20 μl aliquot in HE buffer. To ensure uniform coverage of the bottom of the well the plate was briefly spun at 3000×g. To start the reaction NADPH and DTNB were added as a 20 μl aliquot in HE buffer and the plate was moved to the plate reader preheated to 37° C. The optical density at 405 nm was measured every 10 sec and initial linear reaction rates measured.

These compounds were identified as inhibitors of thioredoxin reductase and they were tested for cytotoxicity in the NCI's human cancer cell line panel of 60 human cancer lines (Monks et al., 1991). The IV-2 and DLK-36, which we have shown to be inhibitors of thioredoxin reductase with Ki values of 30.8 RM and 30.9 RM, respectively were used as seed compounds. The COMPARE pattern recognition program was also used to determine a Pearson correlation coefficient in order to rank the similarity of the pattern of growth inhibition caused by compounds from the NCI database of investigational drugs with the patterns of growth inhibition caused by IV-2 and DLK-36. Ninety-two compounds with similar patterns of activity from 50,000 compounds already tested in the cell screen were identified. Of the 92 compounds, 47 were non-discreet and available for further study. The correlation coefficients for the top 100 compounds lay between 0.836 and 0.718. Forty-seven of these compounds were non-discrete and available in sufficient quantities for further testing. As a negative control for the COMPARE evaluation process, an additional 52 nondiscreet compounds were selected based on the lack of correlation between their patterns of cytotoxicity and that of DLK-36. A library of 221 randomly chosen natural products comprising a mixture of plant derived alkaloids and other compounds and pure bacterial products were also tested for their ability to inhibit thioredoxin reductase/thioredoxin-dependent insulin reduction. Stock solutions of the compounds, 10 mg/ml, were made in dimethylsulfoxide and stored at −20° C. Serial dilutions from these stock solutions were made in HE buffer immediately before use. The small amount of dimethylsulfoxide into the assays had no effect on activities. In the initial screen the agents were preincubated at room temperature for 30 minutes with thioredoxin reductase, glutathione reductase or thioredoxin reductase/thioredoxin in a volume of 40 μl after which remaining components of the assay were added as a 20 μl aliquot. The activities of some agents were also evaluated in subsequent assays without the preincubation.

Results: The linearity of all assays was verified with respect to time and to the amounts of glutathione reductase, thioredoxin reductase or thioredoxin. For the thioredoxin reductase/thioredoxin-dependent insulin reduction assay the variance for 12 control assays was ±0.05%. For assays of thioredoxin reductase and glutathione reductase the variance was ±0.18%. Using replicate assays the lower limit for reproducible detection of inhibition is about 5% inhibition.

The 47 compounds having $IC_{50} \leq 50$ μg/ml are shown below in Table I. Of 47 nondiscreet compounds tested in a thioredoxin reductase/thioredoxin insulin reduction assay, 36 (77%) were inhibitors with $IC_{50}s \leq 10$ μg/ml and 15 of those (32%) had $IC_{50}s \leq 1$ μg/ml.

TABLE I

Compounds identified as potential inhibitors of thioredoxin reductase

| NSC# | $IC_{50}$ (μg/ml) in TR/Trx Assay | $GI_{50}$ (μg/ml) All Tumors | $GI_{50}$ (μg/ml) Leukemias |
|---|---|---|---|
| 401005[a] | 0.06 | 7.6 | 1.8 |
| 208731[b] | 0.10 | 0.6 | 0.03 |
| 382000[b] | 0.10 | 1.0 | 0.1 |
| 665103[b] | 0.10 | 0.4 | 0.04 |
| 617145[a] | 0.12 | 4.4 | 0.2 |
| 618605[a] | 0.12 | 7.2 | 2.5 |

TABLE I-continued

Compounds identified as potential inhibitors of thioredoxin reductase

| NSC# | IC$_{50}$ ($\mu$g/ml) in TR/Trx Assay | GI$_{50}$ ($\mu$g/ml) All Tumors | GI$_{50}$ ($\mu$g/ml) Leukemias |
|---|---|---|---|
| 622378[a] | 0.12 | 5.0 | 1.6 |
| 620109[a] | 0.32 | 1.1 | 0.2 |
| 163027[a] | 0.38 | 3.1 | 0.6 |
| 131233[a] | 0.39 | 2.9 | ND |
| 665102[a] | 0.42 | 0.7 | 0.1 |
| 631136[a] | 0.47 | 2.4 | 0.8 |
| 681277[a] | 0.49 | 0.7 | 0.2 |
| 140377[a] | 0.63 | 0.3 | 0.1 |
| 603084[a] | 0.84 | 2.7 | 0.4 |
| 382007[a] | 1.1 | 5.7 | 2.1 |
| 635002[a] | 1.1 | 3.3 | 1.5 |
| 620358[a] | 1.3 | 0.5 | 0.1 |
| 657028[b] | 1.5 | 14.9 | 10.7 |
| 661221[a] | 1.7 | 0.8 | 0.3 |
| 622188[a] | 1.9 | 18.4 | 7.3 |
| 645330[a] | 1.9 | 1.5 | 0.3 |
| 350629[b] | 2.0 | 1.7 | 0.1 |
| 102817[a] | 2.1 | 1.3 | 0.2 |
| 626162[b] | 2.3 | 0.1 | 0.01 |
| 655897[a] | 2.5 | 8.5 | 1.8 |
| 267461[a] | 3.0 | 0.1 | 0.03 |
| 627124[a] | 3.0 | 1.1 | 22.2 |
| 610187[a] | 4.0 | 3.1 | 1.0 |
| 624982[b] | 4.0 | 1.5 | 0.4 |
| 664951[a] | 6.7 | 7.2 | 3.8 |
| 277293[b] | 7.0 | 0.3 | 0.1 |
| 608972[b] | 7.0 | 10.3 | 1.9 |
| 634761[b] | 7.0 | 3.8 | 1.1 |
| 664271[b] | 10.0 | 1.7 | 0.2 |
| 665878[a] | 10.0 | 2.4 | 1.9 |
| 625814[a] | 11.0 | 9.9 | 3.3 |
| 264054[a] | 15.0 | 0.5 | 0.2 |
| 652257[a] | 16.0 | 9.2 | 1.1 |
| 661225[b] | 17.0 | 0.8 | 0.1 |
| 637828[a] | 25.0 | 0.5 | 0.1 |
| 647546[b] | 25.0 | 5.8 | 1.6 |
| 655305[b] | 33.0 | 4.0 | 1.2 |
| 641396[b] | 35.0 | 1.1 | 0.2 |
| 668262[b] | 35.0 | 0.5 | 0.1 |
| 662781[b] | 40.0 | 0.5 | 0.1 |
| 626678[a] | 50.0 | 3.1 | 1.5 |

[a]Compounds identified by COMPARE with seed IV-2
[b]Compounds identified with seed DLK-36

The range of Pearson correlation coefficients compared to the seed compounds IV-2 or DLK-36 for these compounds was 0.836 (NSC 401005) to 0.718 (NSC 603084). The concentration causing 50% inhibition of activity in the thioredoxin reductase/thioredoxin-dependent insulin reduction assay, ranked from the most to the least active compounds, is given. Also given is the mean 50% growth inhibition concentration (GI$_{50}$) of the compounds for the entire cell line panel and for leukemias which was the most sensitive human tumor type.

The structures of the 8 most potent inhibitors IC$_{50}$ TRTrx$\leq$0.15 $\mu$g/ml) in the thioredoxin reductase/thioredoxin-dependent insulin reduction assay are shown below:

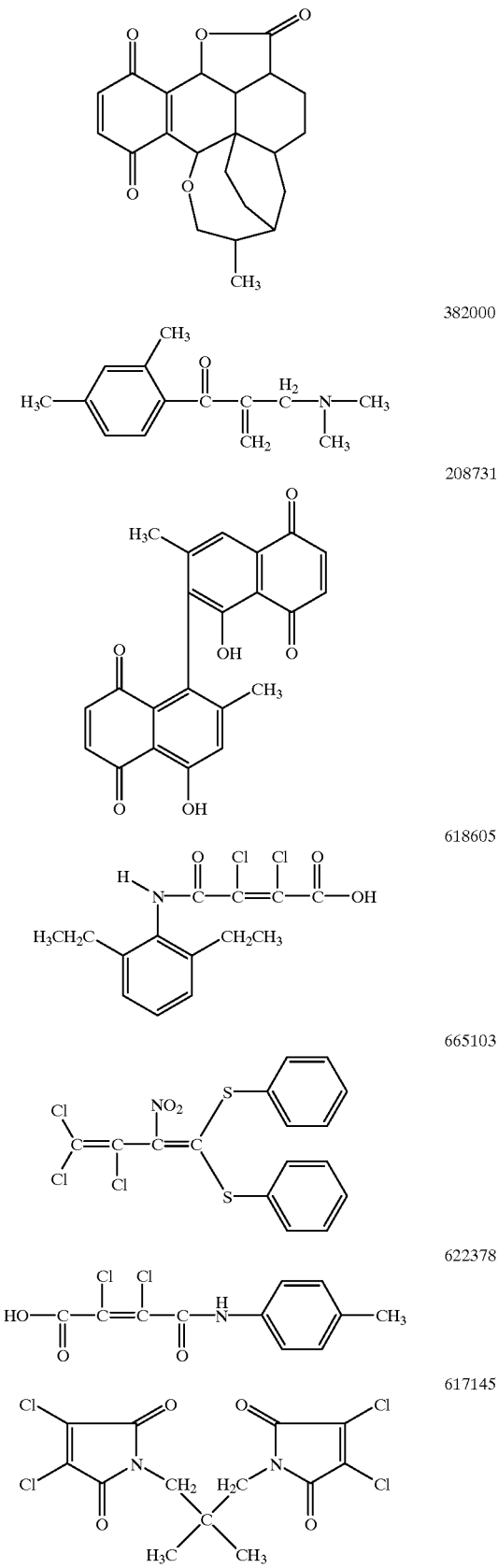

In comparison, a similar screening assay of 52 compounds from the NCI database whose activity was not related to that of the seed compound DLK-36 yielded only 5 compounds (10%) with $IC_{50}s \leq 10$ μg/ml and 1 compound (2%) with an $IC_{50} \leq$ μg/ml. A screening assay of 221 randomly selected pure compounds derived from plant and microbial sources identified 6 compounds (3%) with $IC_{50} \leq 10$ μg/ml and 3 compounds (1.5%) with $IC_{50} \leq 1$ μg/ml.

As secondary screens we used assays of thioredoxin reductase alone, to estimate the contribution of its inhibition to the inhibition seen in the primary screen, and glutathione reductase, to obtain estimates of the specificity of reductase inhibition. This is shown below in Table II:

TABLE II

Selectivity of compounds for thioredoxin reductase, glutathione reductase or thioredoxin

| NSC# | $IC_{50}$TRTrx (μg/ml) | $IC_{50}$GR (μg/ml) | $IC_{50}$TR (μg/ml) | TR/TRT rx | GR/TR |
|---|---|---|---|---|---|
| 401005[a] | 0.06 | 15 | 0.1 | 1.7 | 150 |
| 208731[b] | 0.10 | 5 | 0.1 | 1.0 | 50 |
| 382000[b] | 0.10 | 3 | 0.1 | 1.0 | 30 |
| 665103[b] | 0.10 | 32 | 5 | 50.0 | 6 |
| 617145[a] | 0.12 | 50 | 0.1 | 0.8 | 500 |
| 618605[a] | 0.12 | 34 | 0.1 | 0.8 | 340 |
| 622378[a] | 0.12 | 20 | 0.1 | 0.8 | 200 |
| 620109[a] | 0.32 | 33 | 0.1 | 0.3 | 330 |
| 163027[a] | 0.38 | 40 | 5 | 13.2 | 8 |
| 131233[a] | 0.39 | 30 | 1 | 2.6 | 30 |
| 631136[a] | 0.47 | 70 | 2 | 4.3 | 35 |
| 681277[a] | 0.49 | 33 | 0 | 0.2 | 330 |
| 140377[a] | 0.63 | 15 | 4 | 6.4 | 4 |
| 603084[a] | 0.84 | 15 | 5 | 6.0 | 3 |
| 382007[a] | 1.08 | 3 | 2 | 1.9 | 2 |
| 635002[a] | 1.14 | 20 | 10 | 8.8 | 2 |
| 620358[a] | 1.26 | 30 | 7 | 5.6 | 4 |
| 657028[b] | 1.50 | 28 | 6 | 4.0 | 5 |
| 661221[a] | 1.65 | 34 | 7 | 4.2 | 5 |
| 622188[a] | 1.89 | 80 | 5 | 2.7 | 16 |
| 645330[a] | 1.89 | 50 | 50 | 26.5 | 1 |
| 350629[b] | 2.00 | 35 | 3 | 1.5 | 12 |
| 102817[a] | 2.08 | 50 | 5 | 2.4 | 10 |
| 664951[a] | 6.65 | 35 | 50 | 7.5 | 1 |

[a]Compounds identified by COMPARE with seed IV-2
[b]Compounds identified with seed DLK-36

In Table II, the concentrations of compound causing 50% inhibition of activity in the thioredoxin reductase/thioredoxin-dependent insulin reduction assay ($IC_{50}$-TRTrx), in the thioredoxin reductase assay ($IC_{50}$TR) or in the glutathione reductase assay ($IC_{50}$GR) are given ranked in decreasing order of potency of inhibition of the thioredoxin reductase/thioredoxin-dependent insulin assay. Also given are the ratio of the $IC_{50}$ in the thioredoxin-dependent assay to the $IC_{50}$ in the assay of thioredoxin reductase alone (TR/TRTrx), and the ratio of the $IC_{50}$ in the glutathione reductase assay to the $IC_{50}$ in the thioredoxin reductase assay (GLUTATHIONE REDUCTASE/TR).

Of 24 compounds which were potent inhibitors of thioredoxin reductase/thioredoxin-dependent insulin reduction, 13 were at least 10-fold more selective as inhibitors of thioredoxin reductase compared to glutathione reductase with 6 of the compounds showing 100-fold selectivity. Of the most potent compounds, four show greater than 100 fold selectivity for the ihibition of thioredoxin reductase of versus glutathione reductase (NSC 401005, NSC 617145, NSC 618605 and NSC 622378). Additionally, the following compounds (NSC 620109 and 681277) show greater than 100 fold selectivity for the inhbition of thioredoxin reductase of versus glutathione reductase.

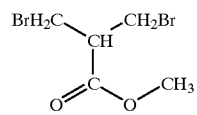

620109

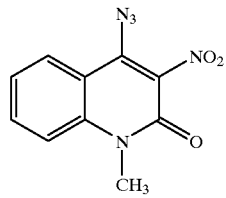

681277

In addition, many of the compounds identified appeared to be specific for either thioredoxin reductase or thioredoxin (including its interaction with thiredoxin reductase).

There were several compounds that, while active in the thioredoxin reductase/thioredoxin-dependent insulin assay, did not inhibit thioredoxin reductase alone suggesting that these compounds inhibit thioredoxin. These compounds include NSC 665103 (shown above), NSC 645330, and NSC 163027 (both of which are shown below):

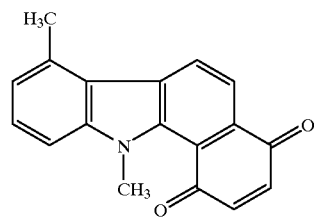

645330

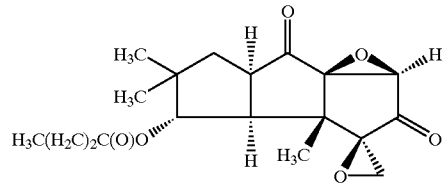

163027

In the NCI cell line panel the sensitivity of the leukemias to growth inhibition by the selected compounds was consistently greater than the mean sensitivity of all the cell lines (see Table II). A number of the compounds showed patterns of selective growth inhibition for colon, renal and breast cancer cell lines (data not shown).

The compounds of the present invention may identify other structures (i.e. related compounds) which inhibit thioredoxin/thioredoxin reductase.

Although not wishing to be bound by theory, a commonality appears exist among the structures of the compounds which inhibited thioredoxin reductase/thioredoxin-dependent insulin reduction. This commonality appears to be the α-β-unsaturated keto moiety with highly electron-deficient centers. The high degree of halogenation of a number of these agents may also contribute to their reactivity. Apart from the ability of these electron deficient moieties to target the thiol functions of thioredoxin reductase and thioredoxin, the specificity of the agent for inhibition may arise from interaction of the multiple carbonyl functions with positively charged histidine, or e-amino residues of lysine.

The method of this invention involves administering to a mammalian host, preferably a human host, pharmacologically effective amounts of one inhibitor of redox signaling. The inhibitors (i.e. the NSC compounds described above), may be combined in vitro before administration or separately administered to the host with other anticancer agents, in either order or concurrently or simultaneously, with administration generally taking place up to 24 hours after the administration of the other biological active agent(s).

The administration(s) may take place by any suitable technique, including oral, subcutaneous and parenteral administration, preferably parenteral or oral. Examples of parenteral administration include intravenous, intraarterial, intramuscular, and intraperitoneal, with intraperitoneal and intravenous being preferred. The dose and dosage regimen will depend mainly on whether the inhibitors are being administered for therapeutic or prophylactic purposes, separately or as a mixture, the type of biological damage and host, the history of the host, and the type of inhibitors or biologically active agent. The amount must be effective to achieve an enhanced therapeutic index as defined above. It is noted that humans are treated longer than the mice and rats with a length proportional to the length of the disease process and drug effectiveness. The doses may be single doses or multiple doses over a period of several days, but single doses are preferred. For purposes herein, a protection level of at least 50% means that at least 50% of the treated hosts exhibit improvement against the disease or infection, including but not limited to improved survival rate, more rapid recovery, or improvement or elimination of symptoms. The doses may be single doses or multiple doses. If multiple doses are employed, as preferred, the frequency of administration will depend, for example, on the type of host and type of cancer, dosage amounts, etc. For some types of cancers or cancer lines, daily administration may be effective, whereas for others, administration every other day or every third day may be effective, but daily administration ineffective. The practitioner will be able to ascertain upon routine experimentation which route of administration and frequency of administration are most effective in any particular case. The dosage amounts for cancer which appear to be most effective herein are those that result in regression in size of the tumor or complete disappearance or non-reappearance of the tumor, and are not toxic or are acceptably toxic to the host patient. Generally, such conditions as fever, chills and general malaise are considered acceptable. The optimum dose levels may also depend on sequence of administration, existing tumor burden, are the type of precursor.

Compounds and agents of the present invention, in conjunction with a pharmaceutically acceptable carrier, may be used for any of the therapeutic effects, discussed above. Such compositions may be in the form of an agent in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

This embodiment of the invention relates to the administration of a pharmaceutical composition (an inhibitor), in conjunction with a pharmaceutically acceptable carrier, for any of the therapeutic effects discussed above.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.) hereby incorporated herein by reference in its entirety.

Pharmaceutical compositions for oral administration can be formulated using pharmaceutically acceptable carriers well known in the art in dosages suitable for oral administration Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyimethylcellulose, or sodium c arboxymethylcelluiose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound. i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers, Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxyrnethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition, For administration of TR/Trx inhibitors, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and herein as well as generally available to practitioners in the art.

The NSC composition which inhibit thioredoxin and/or thioredoxin reductase and induces apoptosis, will enhance the antitumor activity of clinically used anticancer agents by contributing to tumor cell killing. This will enhance the antitumor activity of the clinical agent, especially for those agents where tumor cells have become resistant to the antitumor agent through their elevated levels of thioredoxin and/or the lack of ability to apoptose. Therefore, in another embodiment, the NSC compounds may be administered in combination which clinically available agents used to treat cancer. These may include, but are not limited to, cisplatin, doxorubicin, etoposide, taxol, taxotere, tamoxifen, IL-2, methotrexate, and 5-fluorouracil.

Tissue with elevated levels of thioredoxin may lose the ability to eliminate damaged cells through the process of apoptosis and therefore may lead to the development of cancer.

Therefore, in one embodiment, the NSC composition which inhibit thioredoxin and induce apoptosis, may be administered on a regular basis to induce apoptosis for the prevention of cancer.

Based on the measured in vivo treatment doses of the disulfides (IV-2, DLK-36), Table III shows the expected preferred IP dose ranges.

TABLE III

In vivo treatment doses

| Compound | in vitro IC$_{50}$ TR/Trx (µg/ml) | Dose in vivo treatment dose (mg/kg/day) for 14 days | Dose Projected in vivo treatment range (mg/kg/day) | T/C % tumor volume at day 28 |
|---|---|---|---|---|
| IV-2 | 7 | 5 | — | 56.7 |
|  | 7 | 10 | — | 45.9 |
|  | 7 | 15 | — | 2.3 |
| DLK-36 | 40 | 25 | — | 100.7 |
|  | 40 | 40 | — | 23.7 |
| 401005 | ≦0.1 | — | 0.01–5 | — |
| 208731 | ≦0.1 | — | 0.01–5 | — |
| 382000 | ≦0.1 | — | 0.01–5 | — |
| 665103 | ≦0.1 | — | 0.01–5 | — |
| 617145 | ≦0.5 | — | 0.05–25 | — |
| 618605 | ≦0.5 | — | 0.05–25 | — |
| 622378 | ≦0.5 | — | 0.05–25 | — |
| 620109 | ≦0.5 | — | 0.05–25 | — |
| 163027 | ≦0.5 | — | 0.05–25 | — |
| 131233 | ≦0.5 | — | 0.05–25 | — |
| 665102 | ≦0.5 | — | 0.05–25 | — |
| 631136 | ≦0.5 | — | 0.05–25 | — |
| 681277 | ≦0.5 | — | 0.05–25 | — |
| 140377 | ≦1.0 | — | 0.1–50 | — |
| 382007 | ≦5.0 | — | 0.5–250 | — |
| 635002 | ≦5.0 | — | 0.5–250 | — |
| 620358 | ≦5.0 | — | 0.5–250 | — |
| 657028 | ≦5.0 | — | 0.5–250 | — |
| 661221 | ≦5.0 | — | 0.5–250 | — |
| 622188 | ≦5.0 | — | 0.5–250 | — |
| 645330 | ≦5.0 | — | 0.5–250 | — |
| 350629 | ≦5.0 | — | 0.5–250 | — |
| 102817 | ≦5.0 | — | 0.5–250 | — |
| 626162 | ≦5.0 | — | 0.5–250 | — |
| 655897 | ≦5.0 | — | 0.5–250 | — |
| 267124 | ≦5.0 | — | 0.5–250 | — |
| 610187 | ≦5.0 | — | 0.5–250 | — |
| 624982 | ≦5.0 | — | 0.5–250 | — |
| 664951 | ≦10.0 | — | 1–500 | — |
| 277293 | ≦10.0 | — | 1–500 | — |
| 608972 | ≦10.0 | — | 1–500 | — |
| 634761 | ≦10.0 | — | 1–500 | — |
| 664271 | ≦10.0 | — | 1–500 | — |
| 665878 | ≦10.0 | — | 1–500 | — |

It is anticipated that as the understanding of cellular redox stated and its role in the control of cell growth advances, new targets for anticaner drug development will emerge. There is compelling evidence from in vitro studies that alterations in the redox state of proteins involving key cysteine residues can lead to conformation changes that affect the protein's biological factor. The link between external stimuli and activation of growth, cell death and transformation, through redox modulation is growing. The possibility of reversing the uncontrolled growth of tumors through control of redox signaling, or committing a cell to die by the redox regulation of factors involved in cell death provide intriguing prospects for future drug development.

While the foregoing has been set forth in considerable detail, the sequences are presented for elucidation, and not limitation. Modifications and impovements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein.

What is claimed is:

1. A method of ihibiting a thioredoxin/thioredoxin reductase redox system in a cell comprised of contacting said cell with an effective amount of an agent that is an inhibitor of redox activity, said inhibitor having an $IC_{50}$ TR/Trx of less than about 50 µg/ml and being selected from the group consisting of NSC 401005, NSC 208731, NSC 382000, NSC 665103, NSC 617145, NSC 618605, NSC 622378, NSC 620109, NSC 163027, NSC 131233, NSC 665102, NSC 631136, NSC 681277, NSC 140377, NSC 603084, NSC 382007, NSC 635002, NSC 620358, NSC 657028, NSC 661211, NSC 622188, NSC 645330, NSC 350629, NSC 102817, NSC 626162, NSC 655897, NSC 267461, NSC 627124, NSC 610187, NSC 624982, NSC 664951, NSC 277293, NSC 608972, NSC 634761, NSC 664271, NSC 665878 and NSC 625814.

2. The method of claim 1, wherein said agent prevents inhibition of apoptosis.

3. A method of inhibiting a thioredoxin/thioredoxin reductase redox system in a cell comprised of contacting said cell with an effective amount of an inhibitor of redox activity, wherein said inhibitor is NSC 631136.

4. A method of inhibiting a thioredoxin/thioredoxin reductase redox system in a cell comprised of contacting said cell with an effective amount of an inhibitor of redox activity, wherein said inhibitor is NSC 401005.

* * * * *